US010712346B2

(12) United States Patent
Tsuji et al.

(10) Patent No.: US 10,712,346 B2
(45) Date of Patent: Jul. 14, 2020

(54) INTRACELLULAR DELIVERY VEHICLE

(71) Applicants: KIRIN KABUSHIKI KAISHA, Tokyo-to (JP); THE UNIVERSITY OF TOKYO, Tokyo (JP); TOHOKU UNIVERSITY, Sendai-shi, Miyagi (JP)

(72) Inventors: Toshikazu Tsuji, Tokyo (JP); Kumiko Ikado, Tokyo (JP); Sayuri Yamada, Tokyo (JP); Seiichi Uchiyama, Tokyo-to (JP); Kyoko Kawamoto, Tokyo-to (JP); Hidetoshi Tokuyama, Sendai (JP); Kentaro Okano, Sendai (JP)

(73) Assignees: KIRIN HOLDINGS KABUSHIKI KAISHA, Nakano-ku, Tokyo (JP); THE UNIVERSITY OF TOKYO, Bunkyo-ku, Tokyo (JP); TOHOKU UNIVERSITY, Sendai-shi, Miyagi (JP)

( * ) Notice: Subject to any disclaimer, the term of this patent is extended or adjusted under 35 U.S.C. 154(b) by 142 days.

(21) Appl. No.: 15/756,677

(22) PCT Filed: Sep. 6, 2016

(86) PCT No.: PCT/JP2016/076175
§ 371 (c)(1),
(2) Date: Mar. 1, 2018

(87) PCT Pub. No.: WO2017/043484
PCT Pub. Date: Mar. 16, 2017

(65) Prior Publication Data
US 2019/0137503 A1 May 9, 2019

(30) Foreign Application Priority Data

Sep. 7, 2015 (JP) ................. 2015-176106

(51) Int. Cl.
*C07D 233/04* (2006.01)
*G01N 33/58* (2006.01)
*C07D 233/24* (2006.01)
*C08F 222/10* (2006.01)
*A61K 9/51* (2006.01)
*C08F 122/38* (2006.01)
*C08F 212/12* (2006.01)
*C08F 297/00* (2006.01)
*C08F 212/08* (2006.01)
*C08F 220/54* (2006.01)

(52) U.S. Cl.
CPC ......... *G01N 33/582* (2013.01); *A61K 9/5138* (2013.01); *C07D 233/24* (2013.01); *C08F 122/385* (2013.01); *C08F 212/12* (2013.01); *C08F 222/1006* (2013.01); *C08F 297/00* (2013.01); *C08F 212/08* (2013.01); *C08F 220/54* (2013.01); *C08F 222/102* (2020.02); *C08F 2438/00* (2013.01)

(58) Field of Classification Search
CPC ............................ C07D 233/04; C07D 233/06
See application file for complete search history.

(56) References Cited

U.S. PATENT DOCUMENTS

| 5,853,694 A | 12/1998 | Engberts et al. |
| 7,115,683 B2 * | 10/2006 | Kim ............ B82Y 30/00 524/789 |
| 2012/0076853 A1 | 3/2012 | Taylor et al. |

FOREIGN PATENT DOCUMENTS

| DE | 3239091 A1 * | 4/1984 | ........... C08F 2/22 |
| EP | 107 145 A2 * | 5/1984 | ........... C08F 4/04 |
| JP | 2001-187764 * | 7/2001 | ........... C07C 69/40 |
| JP | 2004-49214 A | 2/2004 | |
| JP | 2005-68120 A | 3/2005 | |
| JP | 2005517054 A | 6/2005 | |
| JP | 2011-157503 A | 8/2011 | |
| JP | 2012-521398 A | 9/2012 | |
| JP | 2013-256531 A | 12/2013 | |
| KR | 100484726 B1 | 4/2005 | |
| WO | 03066686 A1 | 8/2003 | |
| WO | 2013/094748 A1 | 6/2013 | |

OTHER PUBLICATIONS

EP 107 145 (May 2, 1984) Rahlwes et al.; machine translation. (Year: 1984).*
JP 2001-187764 (Jul. 10, 2001); machine translation. (Year: 2001).*
Mitsuo Sawamoto, "Modern Cationic Vinyl Polymerization", Prog. Polym. Sci., vol. 16, No. 1, pp. 111-172, 1991, 62 pages total.
Extended European Search Report, dated Feb. 20, 2019, issued by the European Patent Office in counterpart European Patent Application No. 16844345.5.
Communication, dated Apr. 19, 2019, issued by the Japanese Patent Office in counterpart Japanese Application No. 2015-176106.
Toshikazu Tsuji, et al., "Cationic Fluorescent Polymeric Thermometers with the Ability to Enter Yeast and Mammalian Cells for Practical Intracellular Temperature Measurements", Analytical Chemistry, 2013, pp. 9815-9823, vol. 85.
Teruyuki Hayashi, et al., A Cell-Permeable Fluorescent Polymeric Thermometer for Intracellular Temperature Mapping in Mammalian Cell Lines, PLOS ONE, Feb. 2015, pp. 1-18, vol. 10, No. 2.
Seiichi Uchiyama, et al., "A cationic fluorescent polymeric thermometer for the ratiometric sensing of intracellular temperature", Analyst, May 2015, pp. 4498-4506, vol. 140.
Toshinobu Seki, "Enhancement of Insulin Absorption through Mucosal Membranes Using Cationic Polymers", Yakugaku Zasshi, 2010, pp. 1115-1121, vol. 130, No. 9.

(Continued)

Primary Examiner — Rip A Lee
(74) Attorney, Agent, or Firm — Sughrue Mion, PLLC

(57) ABSTRACT

An intracellular delivery vehicle of which surface is covered by a positive charge, an intracellular delivery complex in which a component or compound desired is loaded in the intracellular delivery vehicle, a temperature-sensitive probe comprising the intracellular delivery complex, and a method for measuring the intracellular temperature by the temperature-sensitive probe are disclosed. The intracellular delivery vehicle is useful on account of its capability of easily delivering the component or compound desired inside the cell without inhibiting cell proliferation.

8 Claims, 13 Drawing Sheets

(56) References Cited

OTHER PUBLICATIONS

Borja Ballarin-Gonzalez, et al., Polycation-based nanoparticle delivery of RNAi therapeutics: Adverse effects and solutions, Advanced Drug Delivery Reviews, 2012, pp. 1717-1729, vol. 64.
Takayuki Imoto, et al., "Preparation and Unique pH-Responsive Properties of Novel Biodegradable Nanocapsules Composed of Poly(y-glutamic acid) and Chitosan as Weak Polyelectrolytes", Macromolecular Bioscience, 2010, pp. 271-277, No. 10.
Joji Mitamura, et al, "Development of New Cationic Surfactant "AG" and application for Hair Conditioners", J. Soc. Cosmet. Chem. Japan, 1996, pp. 84-93, vol. 30, No. 1.
International Search Report for PCT/JP2016/076175 dated Dec. 6, 2016 [PCT/ISA/210].
International Preliminary Report on Patentability, dated Mar. 22, 2018, issued in counterpart International Application No. PCT/JP2016/076175.
Notice of Reasons for Refusal dated Jul. 12, 2019, issued by the Japanese Patent Office in application No. 2015-176106.
Communication, dated Oct. 11, 2019, issued by the Korean Intellectual Property Office in counterpart Application No. 10-2018-7009510.

\* cited by examiner

INTRACELLULAR DELIVERY VEHICLE

CROSS-REFERENCE TO RELATED APPLICATION

The present application claims priority to Japanese Patent Application No. 2015-176106 (filing date: Sep. 7, 2015) which is a prior application applied to Japan. The entire contents of the prior application are incorporated by reference herein.

FIELD OF THE INVENTION

The present invention relates to an intracellular delivery vehicle that allows easy delivery of a desired component or compound into a cell without inhibiting cell proliferation, and a method for production thereof and a method for use thereof.

BACKGROUND ART

It is known that when delivering a protein and the like into a cell, they can be efficiently introduced by cationizing the protein (patent document 1). In addition, it is known that when a peptidic pharmaceutical such as insulin is used in combination with a cationic macromolecule and the like such as chitosan, promotion of mucosal absorption can be devised without damaging mucosal epithelial cells (non-patent document 1). Additionally, issues on side effects of RNAi treatment that introduce siRNA to a cell by nanoparticles using polycations, and solutions to them were discussed (non-patent document 2). Moreover, in recent years, cationic polymers for being introduced into a cell as a temperature-sensitive fluorescence probe have been reported (patent document 2). However, mechanism of cations inducing the above phenomena, their effects on the cell, and their range of applications, have not necessarily been clarified.

Beside them, a number of works for development of functions focusing on cations have been done. For example, it was found that nano capsules composed of cation-based biopolymer chitosan and γ-glutamic acid have a character that swell/shrink in conjunction with the surrounding pH, and its applications are investigated (non-patent document 3). In addition, a possibility of application of a new type of cation activator to hair conditioners (non-patent document 4), or application of the cationic polymers that have exceptionally low absorption while retaining charge quantity (patent document 3) have been reported.

However, although various cationic polymers can be provided by these technologies, it has been difficult to select polymers that could be easily introduced inside a cell without inhibiting cell proliferation, especially not inhibiting cell division of the cell to which the polymers are introduced.

PRIOR ART DOCUMENT

Non Patent Document

[Non patent document 1] Toshinobu Seki, YAKUGAKU ZASSHI, vol. 130 (9), pp. 1115-1121, 2010
[Non patent document 2] Borja Ballarin-Gonzalez et. al., Advanced Drug Delivery Reviews vol., 64 p. 1717-1729, 2012
[Non patent document 3] Takayuki Imoto et. al., Macromol. Biosci. Vol. 10, pp. 271-277, 2010
[Non patent document 4] Joji Mitamura et al., J. Soc. Cosmet. Chem. Jpn. Vol. 30(1), pp. 84-93, 1996

Patent Document

[Patent document 1] JP 2004-49214 A
[Patent document 2] WO 2013/094748
[Patent document 3] JP 2011-157503 A

SUMMARY OF THE INVENTION

A purpose of the present invention is to provide a vehicle that easily delivers a desired component or compound intracellularly without inhibiting cell proliferation, and a method for production thereof and a method for use thereof.

In a process of developing a technology to intracellularly introduce a temperature-sensitive fluorescence probe, the inventors have discovered a method for preparing a novel vehicle that can be easily introduced into a cell and yet does not inhibit cell division of the cell in which the vehicle is introduced. The present invention is based on this finding.

Therefore, the present invention includes the following inventions:
(1) A intracellular delivery vehicle, of which surface is covered by a positive charge.
(2) An intracellular delivery complex, wherein a component or compound desired to be delivered inside a cell is loaded in the intracellular delivery vehicle according to (1).
(3) The intracellular delivery complex according to (2), wherein said component or compound desired to be delivered into the cell is covalently bonded to the intracellular delivery vehicle.
(4) The intracellular delivery complex according to (2) or (3), wherein the compound is a heat-sensitive unit which changes its character in response to the temperature, and a fluorescent unit which changes fluorescence intensity or lifetime in relation to the character change of the heat-sensitive unit.
(5) A temperature-sensitive probe, comprising the intracellular delivery complex according to (4).
(6) A method for measuring intracellular temperature, comprising the steps of:
(a) introducing the temperature-sensitive probe according to (5) into a cell; and
(b) measuring fluorescence intensity or fluorescence lifetime under irradiation of excitation light.

An advantage of the present invention is that it is possible to introduce a desired component or compound into a cell with ease, without a need of complicated processes such as microinjection. Another advantage is that the introduced vehicle does not inhibit cell proliferation. In addition, an advantage is that, by using the vehicle of the invention, the desired component or compound can be easily delivered into the cell without inhibiting cell proliferation. Moreover, from the examples in this description, it was also confirmed that the present invention has an advantage that vehicle of the present invention does not inhibit cell differentiation when introduced into the cell.

DETAILED DESCRIPTION OF THE INVENTION

1. Definition

Figure 1:
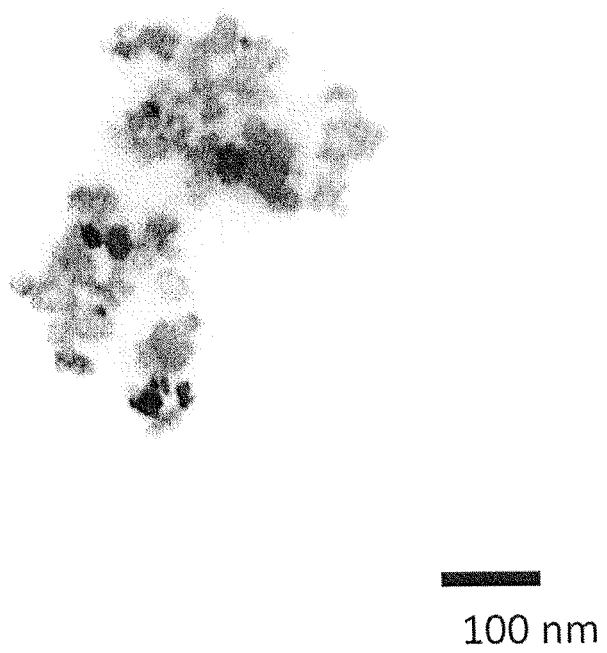
FIG. 1 An example of the result of the observation of compound 2b by TEM.

In the present invention, "vehicle" represents a medium or a carrier that delivers a desired component or compound into a cell.

In the present invention, "cell" includes both prokaryotic and eukaryotic cells as commonly categorized, and is not limited to specific species of organisms. For example, prokaryotic cells are classified to eubacteria and archaea, and in particular, eubacteria are classified to gram-positive bacteria such as actinobacteria and gram-negative bacteria such as proteobacteria, and the scope of application of the intracellular delivery vehicle in the present invention is not limited based on the thickness of the peptidoglycan layer and the like. On the other hand, eukaryotic cells mainly apply to cells that belong to eukaryotes (protozoa, fungi, plants, and animals). For example, yeasts, which are generally used for research in molecular biology as well as used industrially, belong to fungus. In addition, the intracellular delivery vehicles of the present invention are favorably applied to both floating and adherent cells.

"$C_{1-3}$ alkyl" in the present description means a linear chain, branched chain or cyclic alkyl group having 1-3 carbon atoms, and includes methyl group, ethyl group, n-propyl group, i-propyl group and cyclopropyl group.

"$C_{1-6}$ alkyl" in the present description means a linear chain, branched chain, cyclic or partially cyclic alkyl group having 1-6 carbon atoms, and includes, for example, methyl group, ethyl group, n-propyl group, i-propyl group, n-butyl group, s-butyl group, i-butyl group, t-butyl group, n-pentyl group, 3-methylbutyl group, 2-methylbutyl group, 1-methylbutyl group, 1-ethylpropyl group, n-hexyl group, 4-methylpentyl group, 3-methylpentyl group, 2-methylpentyl group, 1-methylpentyl group, 3-ethylbutyl group and 2-ethylbutyl group; cyclopropyl group, cyclobutyl group, cyclopentyl group, cyclohexyl group, cyclopropylmethyl group and the like, and also includes, for example, $C_{1-4}$ alkyl group, $C_{1-3}$ alkyl group and the like.

"$C_{1-10}$alkyl" in the present description means a linear chain, branched chain, cyclic or partially cyclic alkyl group having 1-10 carbon atoms, and includes, for example, $C_{1-6}$ alkyl group and $C_{1-3}$ alkyl group, which are already defined, and the like.

"$C_{1-20}$ alkyl" in the present description means a linear chain, branched chain, cyclic or partially cyclic alkyl group having 1-20 carbon atoms, and includes, for example, $C_{1-10}$ alkyl group, $C_{1-6}$ alkyl group and $C_{1-3}$ alkyl group, which are already defined, and the like.

"$C_{1-6}$ alkoxy" in the present description means an alkyloxy group containing as alkyl moiety an alkyl group having 1-6 carbon atoms, which are already defined, and includes, for example, methoxy group, ethoxy group, n-propoxy group, i-propoxy group, n-butoxy group, s-butoxy group, i-butoxy group, t-butoxy group, n-pentoxy group, 3-methylbutoxy group, 2-methylbutoxy group, 1-methylbutoxy group, 1-ethylpropoxy group, n-hexyloxy group, 4-methylpentoxy group, 3-methylpentoxy group, 2-methylpentoxy group, 1-methylpentoxy group, 3-ethylbutoxy group, cyclopentyloxy group, cyclohexyloxy group, cyclopropylmethyloxy group and the like, and also includes, for example, $C_{1-4}$ alkoxy group and $C_{1-3}$ alkoxy group and the like.

"Aryl" in the present description means a 6-10 membered aromatic carbocyclic group, and includes, for example, phenyl group, 1-naphthyl group, 2-naphthyl group and the like.

"$C_{7-14}$ aralkyl" in the present description means an arylalkyl group containing aryl group and having 7-14 carbon atoms, and includes, for example, benzyl group, 1-phenethyl group, 2-phenethyl group, 1-naphthylmethyl group, 2-naphthylmethyl group and the like.

Halogen atom in the present description includes, for example, fluorine atom, chlorine atom, bromine atom and iodine atom and the like.

"$C_{1-20}$ alkylene" in the present description means a linear chain, branched chain, cyclic or partially cyclic alkylene group having 1-20 carbon atoms, and includes, for example, methylene group, ethylene group, propylene group, butylene group and the like, and further $C_{1-10}$ alkylene group and $C_{1-6}$ alkylene group and the like.

"$C_{3-20}$ alkenylene" in the present description means a linear chain, branched chain, cyclic or partially cyclic alkenylene group having 3-20 carbon atoms, and includes, for example, propenylene group, butenylene group and the like, and further $C_{3-10}$ alkenylene group, $C_{3-6}$ alkenylene group and the like.

"$C_{3-20}$ alkynylene" in the present description means a linear chain, branched chain, cyclic or partially cyclic alkynylene group having 3-20 carbon atoms, and includes, for example, propynylene group, butynylene group and the like, and further $C_{3-10}$ alkynylene group, $C_{3-6}$ alkynylene group and the like.

"$C_{1-6}$ alkylthio" in the present description means an alkylthio group containing as alkyl moiety an alkyl group having 1-6 carbon atoms, which is already defined, and includes, for example, methylthio group, ethylthio group, n-propylthio group, i-propylthio group, n-butylthio group, s-butylthio group, i-butylthio group, t-butylthio group and the like.

"$C_{1-6}$ alkylsulfinyl" in the present description means an alkylsulfinyl group containing as alkyl moiety an alkyl group having 1-6 carbon atoms, which is already defined, and includes, for example, methylsulfinyl group, ethyl sulfinyl group, n-propylsulphinyl group, i-propylsulfinyl group, n-butylsulfinyl group, s-butylsulfinyl group, i-butylsulfinyl group, t-butylsulfinyl group and the like.

"$C_{1-6}$ alkylsulfonyl" in the present description means an alkylsulfonyl group containing as alkyl moiety an alkyl group having 1-6 carbon atoms, which is already defined, and includes, for example, methylsulfonyl group, ethylsulfonyl group, n-propylsulfonyl group, i-propylsulfonyl group, n-butylsulfonyl group, s-butylsulfonyl group, i-butylsulfonyl group, t-butylsulfonyl group and the like.

"6-18 membered aromatic carbocyclic group" in the present description includes, for example, phenyl group, naphthyl group, anthracenyl group, pyrenyl group, indanyl group, tetralinyl group and the like.

"5-18 membered aromatic heterocyclic group" in the present description means an aromatic heterocycle containing one or more hetero atoms selected from oxygen, nitrogen and sulfur, and includes, for example, pyrrolyl group, pyrazolyl group, imidazolyl group, pyridyl group, indolyl group, quinolyl group, quinoxalinyl group, quinazolinyl group, benzofuranyl group, benzothienyl group, benzopyranyl group, benzochromenyl group and the like.

"$C_{2-6}$ alkenylsulfonyl" in the present description means an alkenylsulfonyl group containing as alkenyl moiety a $C_{2-6}$ alkenyl group, which is already defined, and includes, for example, vinylsulfonyl group, allylsulfonyl group and the like.

"$C_{2-6}$ alkenylcarbonyl" in the present description means an alkenylcarbonyl group containing as alkenyl moiety a $C_{2-6}$ alkenyl group, which is already defined, and includes, for example, acryloyl group, methacryloyl group and the like.

"$C_{2-6}$ alkynylcarbonyl" in the present description means an alkynylcarbonyl group containing as alkynyl moiety a $C_{2-6}$ alkynyl group, which is already defined, and includes, for example, ethynylcarbonyl group and the like.

"$C_{1-6}$ alkylcarbonyl" in the present description means —CO($C_{1-6}$ alkyl) group, wherein the $C_{1-6}$ alkyl group is as already defined.

"$C_{1-6}$ alkoxycarbonyl" in the present description means —CO($C_{1-6}$ alkoxy) group, wherein the $C_{1-6}$ alkoxy group is as already defined.

"$C_{1-6}$ alkyl carbonylamino" in the present description means —NHCO($C_{1-6}$ alkyl) group, wherein the $C_{1-6}$ alkyl group is as already defined.

"$C_{1-6}$ arylcarbonylamino" in the present description means —NHCO(aryl) group, wherein the aryl group is as already defined.

"5-7 membered nitrogen-containing heterocycle" in the present description includes, for example, saturated heterocycle such as pyrrole ring, pyrrolidine ring, piperidine ring, homopiperidine ring, piperazine ring, homopiperazine ring, morpholine ring, thiomorpholine ring and the like.

"4-8 membered nitrogen-containing heterocycle" in the present description includes, for example, pyrrole ring, azetidine ring, pyrrolidine ring, piperidine ring, homopiperidine ring, piperazine ring, homopiperazine ring, morpholine ring, thiomorpholine ring and the like, and 5-7 membered nitrogen-containing heterocycle.

"5-7 membered heterocycle containing two nitrogen atoms" in the present description includes, for example, imidazolidine, tetrahydropyrimidine and the like.

In the present description, when O is inserted in an alkylene group at one or more positions, the alkylene chain will include ether linkage in the principal chain, thereby forming a stable structure.

Thus, it is a matter those skilled in the art should easily understand not to bring structures of —O—O— and —O—CH$_2$—O—. The above-mentioned matter also applies when inserting S to an alkylene group.

In the present description, a copolymer is an aggregate of polymer chains formed by mixing and polymerising monomers corresponding to each unit. A polymer is a polymer chain wherein monomer units are bonded and lined.

"Counter anion" in the present description is not limited in particular as long as it is an anion which is usually used as a counter anion of an organic compound in the technical field of organic chemistry, and includes, for example, halide anion (chloride ion, bromide ion, fluoride ion, iodide ion), conjugate base of organic acid (such as acetate ion, trifluoroacetate ion), nitrate ion, sulfate ion, carbonate ion and the like. Preferable counter anion in the present invention includes, for example, trifluoromethane sulfonate ion, chloride ion, nitrate ion and the like.

Note that when a counter anion is bivalent or more, it will form ionic bonds with corresponding number of ionic functional groups as easily understood by those skilled in the art.

Figure 12:
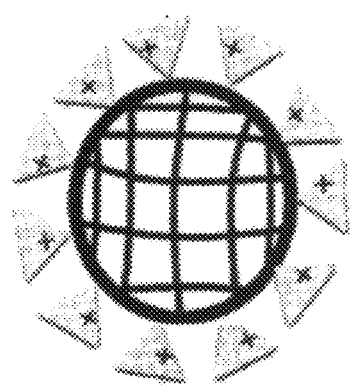
FIG. 12 An example of the intracellular delivery vehicle of the present invention is an arbitrarily shaped gel particle, of which surface is covered with a positive charge.

The shape of the intracellular delivery vehicle of the present invention is preferably substantially a spheroidal shape, and more preferably substantially a spherical shape, as shown in FIG. 12.

The intracellular delivery vehicle can form an intracellular delivery complex by loading a desired component or compound. In addition, the intracellular delivery vehicle can form an intracellular delivery complex by bonding a desired component or compound with a covalent bond. The intracellular delivery vehicle and the intracellular delivery complex can be easily introduced into a cell, and moreover does not inhibit the survival and proliferation of the cell wherein the vehicle complex is introduced. Further, it was confirmed in the examples in the description that the vehicle of the present invention, when introduced in a cell, has an advantage of not inhibiting cell differentiation.

Figure 13:
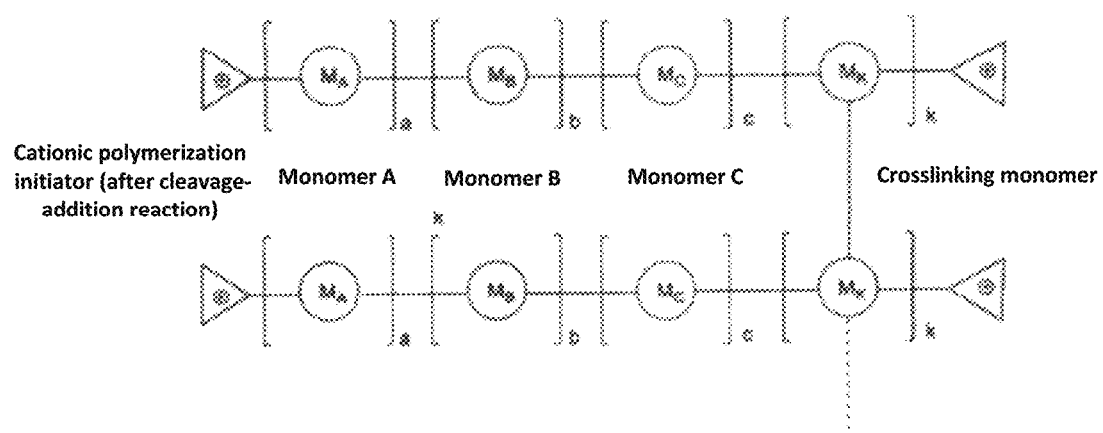
FIG. 13 An example of the structure of the intracellular delivery vehicle in one preferred embodiment of the present invention.

In one preferred embodiment, the intracellular delivery vehicle of the present invention possesses the structure shown in FIG. 13.

3. The Synthetic Method of the Intracellular Delivery Vehicles

The intracellular delivery vehicle of the present invention can be produced by, for example, preparing polymers possessing positive charge on at least one end of the two end units or the units of their vicinity, and crosslinking them intermolecularly. In one preferred embodiment, the intracellular delivery vehicle of the present invention is prepared by conducting radical polymerization reaction using a cationic polymerization initiator, monomers containing carbon-carbon double bonds, and crosslinkers.

(1) Cationic Polymerization Initiator

The cationic polymerization initiators used in the present invention are, (a) stable at room temperature, (b) water soluble, (c) capable of generating radicals that initiate radical polymerization reaction, and (d) possess positive charge under a wide range of pH, or at least around the neutral pH even at the ends of the polymers after the radical polymerization reaction.

Herein, the cationic polymerization initiators preferably maintain their positive charge inside the cells. The pH inside the most cells is 2-9, or 4-8 for the cells of typical animals, plants, and microorganisms. Therefore, the cationic polymerization initiators preferably maintain their positive charge within this pH range.

The cationic polymerization initiator of the present invention has a chemical structure represented by, for example, a general formula (I):

[Chem. 3]

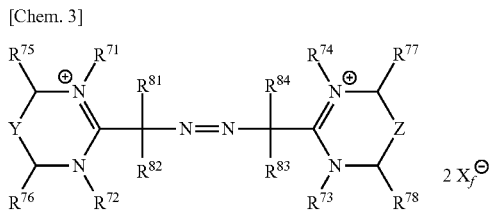

[wherein
Y represents a single bond or $CR^{85}$,
Z represents a single bond or $CR^{86}$,
$R^{72}$, $R^{73}$, $R^{75}$, $R^{76}$, $R^{77}$, $R^{78}$, $R^{85}$ and $R^{86}$ are each independently selected from the group consisting of hydrogen atom, $C_{1-6}$ alkyl group, $C_{1-6}$ alkoxy group, $C_{1-6}$ alkylcarbonyl group, phenyl group and hydroxyl group, wherein said $C_{1-6}$ alkyl group, $C_{1-6}$ alkoxy group, $C_{1-6}$ alkylcarbonyl group and phenyl group are optionally substituted with 1 or 2 substituents selected from the group consisting of $C_{1-6}$ alkyl group, $C_{1-6}$ alkoxy group, $C_{1-6}$ alkylcarbonyl group, phenyl group and hydroxyl group,
$R^{72}$ and $R^{73}$ optionally each independently represent adamanthyl group or $C_{1-6}$ alkyl substituted with $Si(OCH_3)_2(CH_3)$, or $R^{75}$ and $R^{76}$ or $R^{77}$ and $R^{78}$ together optionally form $—(CH_2)_{3-5}—$,
$R^{81}$, $R^{82}$, $R^{83}$ and $R^{84}$ are a substituent selected from the group consisting of $C_{1-4}$ alkyl group, $C_{1-4}$ alkylcarbonyl group and $C_{1-3}$ alkoxy group, wherein the $C_{1-4}$ alkyl group is optionally substituted with one $C_{1-3}$ alkoxy group; and
$R^{71}$ and $R^{74}$ each independently are $C_{1-3}$ alkyl group, and $X_f^-$ is counter anion.]

In one embodiment of the present invention, Y and Z in formula (I) represent a single bond.

In another embodiment, $R^{81}$, $R^{82}$, $R^{83}$ and $R^{84}$ in formula (I) each independently are selected from the group consisting of methyl group, ethyl group, methylcarbonyl group, isobutyl group and 2-methyl-2-methoxy-propyl group.

In another embodiment, $R^{71}$ and $R^{74}$ in formula (I) are methyl group.

In another embodiment, $R^{72}$, $R^{73}$, $R^{75}$, $R^{76}$, $R^{77}$, $R^{78}$, $R^{85}$ and $R^{86}$ in formula (I) each independently are selected from the group consisting of hydrogen atom, $C_{1-6}$ alkyl group, $C_{1-6}$ alkoxy group, $C_{1-6}$ alkylcarbonyl group, phenyl group and hydroxyl group.

In another embodiment, $R^{75}$ and $R^{76}$ or $R^{77}$ and $R^{78}$ in formula (I) together form $—(CH_2)_4—$.

According to a preferred embodiment of the present invention, $R^{72}$ and $R^{73}$, $R^{75}$ and $R^{77}$, $R^{76}$ and $R^{78}$, $R^{81}$ and $R^{84}$, $R^{82}$ and $R^{83}$ and $R^{71}$ and $R^{74}$ in formula (I) each represent the same substituent, and Y and Z represent the same substituent or both a single bond.

According to a more preferable embodiment of a cationic polymerization initiator of the present invention, $R^{71}$, $R^{72}$, $R^{73}$, $R^{74}$, $R^{81}$, $R^{82}$, $R^{83}$ and $R^{84}$ in formula (I) are a methyl group, and $R^{75}$, $R^{76}$, $R^{77}$ and $R^{78}$ are a hydrogen atom, and Y and Z are a single bond.

The synthetic method of the compound of formula (I) is not limited in particular, and it can be synthesized, for example, as follows.

First, dissolve α,α'-azobisisobutyronitrile (AIBN) derivative:

[Chem. 4]

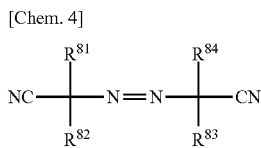

in an appropriate solvent, and by passing hydrogen chloride gas through at room temperature in the presence of an excess of methanol, an active iminoester derivative:

[Chem. 5]

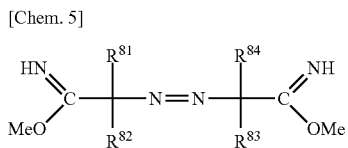

can be obtained. In addition, Me in the structure refers to methyl group in this description. Next, to the iminoester derivative is added an excess of alkylene diamine derivative:

[Chem. 6]

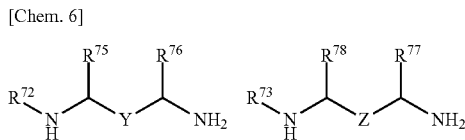

such as ethylene diamine, and by stirring, a compound:

[Chem. 7]

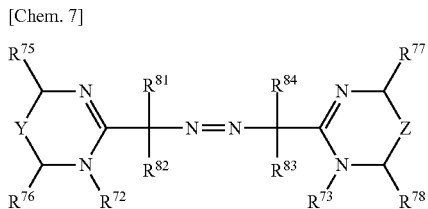

which has a cyclic structure can be obtained. Then, the product is dissolved in dichloromethane and subjected to reaction with 2.1 equivalent of a trifluoromethane sulfonate ester $R^{71}$OTf or $R^{74}$OTf at room temperature under deoxidized conditions, which brings about N-alkylation reaction and the targeted compound presented in formula (I) can be obtained.

The compounds in the above formula (I) are novel compounds, and represent one of the aspects of the present invention.

(2) Monomers

With regards to the monomers, the raw material of the radical polymerization reaction, any compounds having carbon-carbon double bonds can be used. And among them, those skilled in the art can select the ones appropriate for loading or being chemically bonded with the desired components or compounds. Further, among them, those skilled in the art can also select the appropriate ones from the standpoint such as biocompatibility or ease of decomposition. Furthermore, among them, those skilled in the art can select the appropriate ones from the standpoints of reaction efficiency of the radical polymerization reaction, economy, safety, and the like.

In one embodiment of the present invention, for example, in the case where either the component or compound to be loaded is a small molecule with the molecular weight of 1000 or less, a vehicle with a smaller pore-size prepared by increasing the crosslinker concentration can be selected. In addition, since small molecules tend to leach out from the network of the vehicle by diffusion, it is preferable to promote interaction with the vehicle through hydrophobicity, charge, and the like of small molecules, or select monomers capable of directly being bound to the vehicle through covalent bonds, as described in the following. On the other hand, in the case with macromolecules with relatively large molecular weight, controlling the network (pore size) by choosing an appropriate concentration of the crosslinkers can be cited.

In another embodiment, in the case where biocompatibility is a serious concern, use of monomers such as PEG can be cited.

In another embodiment, in the case where the components or compounds to be loaded possess charges, monomers having ionic groups that counter the charge can be selected. For example, if the components or compounds to be loaded have a negative charge, monomers with side chains having a positive charge such as amines can be used, and if the components or compounds to be loaded have a positive charge, monomers with side chains having a negative charge such as carboxylic acids can be used.

In another embodiment, monomers can be selected by the hydrophobicity/hydrophilicity of the components or compounds to be loaded. For example, if the components or compounds to be loaded are highly hydrophobic molecules, monomers not having hydroxyl group, amino group and ionic group in side chains, and having a large number of carbon atoms are selected, and among them, if the components or compounds to be loaded contain a structure having benzene rings, by selecting monomers with side chains having phenyl groups, the loaded component stability inside the vehicles can be maintained through their interactions. On the other hand, in the case where the components or compounds to be loaded are highly hydrophillic molecules and dissolve easily in water, the monomers with side chains containing hydroxyl group, amino group and ionic group are selected.

In another embodiment, in the case where the components or compounds are covalently bound to intracellular delivery vehicles, by synthesizing compounds having the desired small or large molecules covalently bonded to monomers such as the ones acrylamide-based, these compounds can be used as the monomers for these vehicles.

In another embodiment, in the case where releasing of the components or compounds to be loaded out of the vehicle in response to pH is considered, by selecting monomers that change their chemical structures in response to pH, the vehicle's pore size and the strength of their interactions with the components or compounds to be loaded can be controlled. Such monomers include those containing side chains having carboxylic acids and amines.

In another embodiment, in the case where releasing of the components or compounds to be loaded out of the vehicle in response to temperature is considered, by selecting monomers that change their polymer structures in response to temperature, the vehicle's pore size and the strength of their interactions with the components or compounds to be loaded can be controlled. Such monomers include acrylamide-based monomers.

In another embodiment, in the case where releasing of the components or compounds to be loaded out of the vehicles in response to light such as UV light is considered, by selecting monomers in which a part of their structure is cleaved open in response to UV, the structures of the vehicles would be significantly changed allowing the components or compounds to be loaded to be released out of the vehicle. Such monomers include light-cleavable monomers such as PEG-photo-MA (Murayama, Shuhei, et al. "Nano-PARCEL: a method for controlling cellular behavior with external light." Chemical Communications 48.67 (2012): 8380-8382).

(3) Crosslinkers

In terms of crosslinkers for the raw material for radical polymerization reaction, there are no specific limitations as long as they have two or more vinyl groups within the molecule and are commonly used as crosslinkers. More specifically, some examples of the relevant crosslinkers include N,N'-methylenebisacrylamide, N,N'-ethylenebisacrylamide, N,N'-methylenebismethacrylamide, N,N'-ethylenebismethacrylamide, ethyleneglycol diacrylate, ethyleneglycol dimethacrylate, and the like.

The amount of crosslinker used is not particularly specified, but for example, the amount of 0.1-20 mol % can be used for the monomers of the formulas (a), (b), and (c) to be described later.

(4) Reaction Conditions

The intracellular delivery vehicle of the present invention can be synthesized according to the common knowledge in the technical field of macromolecular synthesis, and for example, it can be obtained as a polymer produced by radical polymerization and the like.

Figure 14:
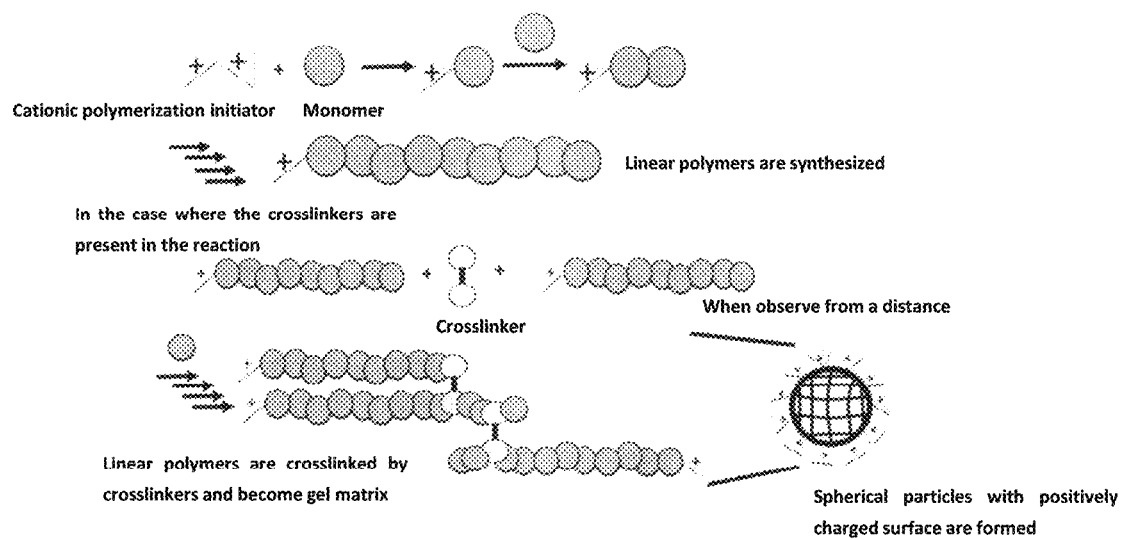
FIG. 14 An example of a typical synthetic method of the intracellular delivery vehicle.

A typical synthetic method of the intracellular delivery vehicle is shown in FIG. 14.

The amount of the polymerization initiator used should be 0.01 mol % or more to the (amount of) monomer used, and an appropriate amount can be selected within the concentration range where the radical polymerization proceeds. For example, the polymerization initiator with 0.1 mol % or more, and more preferably 1 mol % or more can be used.

Solvents used in the polymerization reaction are not particularly specified, and for example, water, dioxane, dimethylformamide, dimethysulfoxide and the like are used. Although not specifically limited, the radical polymerization can be conducted under the conditions including, for example the reaction temperature of 0-100° C., more preferably 50-70° C., and for example, the reaction time of 1-48 hours, more preferably 2-16 hours.

Copolymerization reactions when using the crosslinking monomers can be performed according to the method commonly used in the relevant technical field.

The solvents used in the copolymerization reaction are not particularly specified, and for example, water that contains surfactants (for example, sodium dodecyl sulfate, sodium dodecylbenzene sulfonate, sodium pentadecane sulfate, N-dodecyl-N,N,N-trimethylammonium bromide, N-cetyl-N,N,N-trimethylammonium bromide, TritonX-100, and the like) can be used.

The size of nanogels (the nano-sized gel particles) of the copolymer obtained by using a crosslinker monomer can be controlled by agitation efficiency, reaction temperature, the amount of surfactants used, the amount of reaction initiator used and the amount of crosslinker monomer in the copolymerization reaction. For example, by increasing the amount of the surfactants and/or a reaction initiator, nanogels smaller in size can be obtained. The size of the nanogels to be obtained can be appropriately controlled by those skilled in the art in the field of the present invention, and the size of the nanogels of copolymers of the present invention are, for example, 5-100 nm.

Though not specifically limited, the copolymerization reaction is performed, for example, under the conditions including the reaction temperature of 0-100° C., more preferably 50-70° C., and for example, the reaction time of 1-48 hours, more preferably 2-16 hours.

4. Intracellular Delivery Complex

An intracellular delivery complex can be produced, by loading the desired components or compounds into the intracellular delivery vehicles, or by having the components or compounds bonded to them.
(1) Methods for Producing the Intracellular Delivery Complex, Wherein Said Desired Components or Compounds are Loaded into the Intracellular Delivery Vehicles.

The intracellular delivery complex, wherein said desired components or compounds are loaded into the intracellular delivery vehicle, can be prepared, using a well-known method, as follows.

(i) In the case where the radical polymerization is performed in the presence of the compounds/molecules to be loaded under the polymerization environment as it is, the polymerization can be performed under the conditions of the temperature and solvent, wherein the stability of the compounds/molecules is not be compromised, after employing, for example, emulsion polymerization so that the compounds/molecules are made soluble. Then, by separating the compounds/molecules to be loaded from the vehicles by operations such as centrifugation, dialysis, or filtration, the desired vehicles can be prepared.

(ii) In the case where adsorption is performed by immersing the intracellular delivery vehicles in a solution containing the compounds and the like to be loaded, their adsorption can be promoted by selecting monomers that have strong interaction according to the charges and polarity of the components or compounds to be loaded. It is also possible to enhance the amount of adsorption by controlling the agitation process and temperature. In addition, when using monomers having side chains such as biotin, or if the compound to be loaded is converted to a fusion protein with streptavidin and the like, they will be bound to the vehicles particularly strongly, thereby allowing preparation of stable vehicles from which the compounds to be loaded are hard to leach out.

(iii) In the case where permeation is performed by immersing the intracellular delivery vehicles in a solution containing the compounds and the like to be loaded, by selecting monomers that induce structural changes of the vehicle depending on the pH or temperature, for example, the network structure (pore size) becomes large when immersed and the network structure shrinks after immersing and permeation, thereby allowing the compounds (mainly macromolecules) to be trapped inside the vehicle. Then, by separating compounds/molecules to be loaded from the vehicles, by operations such as centrifugation, dialysis, and filtration, the desired vehicles can be prepared.
(2) Methods for Producing the Intracellular Delivery Complex, Wherein said Desired Components or Compounds are Covalently Bonded to the Intracellular Delivery Vehicles.

The intracellular delivery complex, wherein said desired components or compounds are covalently bonded to the intracellular delivery vehicles can be prepared, using a method well-known to those skilled in the art, as follows.

(i) In the case where the desired components or compounds are bonded to monomers before being polymerized, and then the resulting substance is subjected to radical polymerization reaction, a polymer, which is the vehicle, can be obtained relatively easily under the temperature conditions that promote polymerization. Then, the vehicle can be purified by re-precipitation, filtration, centrifugation, salting out, and the like.

(ii) In the case where the intracellular delivery vehicles are prepared in advance and subsequently the desired components or compounds are bonded to them, the vehicles can be made to bond to compounds by a covalent bond, by attaching a particular activating group to the monomer before polymerization, and subjecting the desired components or compounds having structures specifically reactive to the particular activating group to the reaction with the vehicles after polymerization. For example, a reaction between activated N-hydroxysuccinimide ester and an amino group, or use of a specific bond formation reaction between maleimide group and thiol group can be utilized.
(3) Examples Components and Compounds to be Loaded into the Intracellular Delivery Vehicle The following are preferable examples of the components and compounds to be loaded in the intracellular delivery vehicle of the present invention.

Load insulin to promote percutaneous absorption.
Load skin-whitening or cosmetic components to promote their migration into skin perithelium.
Load dyes for hair coloring agent to enhance their permeability to hair.
Load components good for hair to formulate shampoo and conditioner with them, to enhance their permeability to hair.
Load genetic materials, for devising efficient intracellular delivery of the genetic materials taking advantage of the character of not inhibiting cell proliferation.
Load drugs for devising efficient drug delivery into target cells such as cancer cells.
Load ink to promote stable dispersion of ink components.
(4) A Method of Intracellular Migration of the Intracellular Delivery Complex When introducing the intracellular delivery vehicle of the present invention to a cell, the solution (solvent) is preferably replaced to a solution (solvent) with low ionic strength. Such solvents include water (preferably pure water), aqueous sorbitol solution, and glucose solution. Depending on the type of the cell, a solution such as aqueous glucose solution, and the like, charged with 0.45 mM calcium chloride can also be favorably used.

When introducing the intracellular delivery vehicle to a cell according to the present invention, the concentration of the intracellular delivery vehicle polymer should be prepared such that the final copolymer concentration be 0.001-1% (w/v), more preferably 0.01-0.5% (w/v), which can be mixed with bacterial cells. This applies not only to microbial cells but also to other cells such as adherent cells.

The intracellular delivery complex of the present invention can be introduced into a cell using the method same as above.

5. Cationic Gel-Type Temperature-Sensitive Probes

The intracellular delivery complex of the present invention can also be applied to a temperature-sensitive probe. In such cases, a copolymerization reaction using a heat-sensitive unit, a fluorescent unit, a cationic polymerization initiator, and a crosslinker produces and provides a copolymer used for the temperature-sensitive probe of the present invention.

In terms of combinations of the heat-sensitive unit and the fluorescent unit, any combination of a heat-sensitive unit that changes some characters in response to the surrounding temperature, and a fluorescent unit that changes either the fluorescence intensity or lifetime in response to such character change, can be used. The person skilled in the art can select an appropriate combination depending on the type of cells and the temperature range to be measured. In a preferred embodiment of the present invention, the heat-sensitive units are those that when polymerized, change their shape or hydrophobicity in response to the temperature, for example, molecules having lower or upper limit critical solution temperature (LCST or UCST). For instance, in the case where they show LCST behavior, the polymer chains cohere together by strengthening of intra- or intermolecular hydrophobic bonds at a temperature higher than a certain temperature, and conversely at lower temperature, the polymer chains are bound to water molecules and be hydrated to induce phase transition behavior. The fluorescent units are those that change their fluorescence intensity or lifetime in response to the shape transformation of the heat-sensitive unit. Among the heat-sensitive units, those that change their water solubility due to shape transformation in response to temperature are also known, and in that case, those fluorescent units having solvatochromic character can be used, wherein said fluorescence intensity, fluorescence wavelength or lifetime change depending on the solvent polarity.

(1) Suitable Example of Heat-Sensitive Unit

A suitable example of a heat-sensitive unit included in the copolymer used as a temperature sensitive probe of the present invention has one kind or two kinds or more of repeat structures derived from one kind or two kinds or more of monomers represented by the the following formula (a):

[Chem. 9]

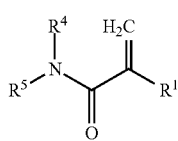

(a)

[wherein $R^1$ is selected from hydrogen atom and $C_{1-3}$ alkyl group;

$R^4$ and $R^5$ are independently selected from hydrogen atom and $C_{1-20}$ alkyl group, wherein the alkyl group is optionally substituted with one or more substituents selected from hydroxyl group, $C_{1-6}$ alkoxy group and aryl group, or $R^4$ and $R^5$, together with nitrogen atom which is bonded to $R^4$ and $R^5$, form a 4-8 membered nitrogen-containing heterocycle, wherein the heterocycle is optionally substituted with one or more substituents selected from $C_{1-6}$ alkyl group, $C_{1-6}$ alkoxy group, nitro group, halogen atom, $C_{1-10}$ alkylcarbonylamino group and arylcarbonylamino group.

(2) Suitable Example of Fluorescent Unit

A suitable example of a fluorescent unit included in the copolymer used as a temperature sensitive probe of the present invention has one kind or two kinds or more of repeat structures derived from one kind or two kinds or more of monomers represented by the following formula (b):

[Chem. 10]

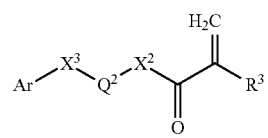

(b)

[wherein $R^3$ is selected from hydrogen atom and $C_{1-3}$ alkyl group;

$X^2$ is O, S or N—$R^{12}$;

$X^3$ is a direct bond, O, S, SO, $SO_2$, N(—$R^{13}$), CON(—$R^{16}$), N(—$R^{16}$)CO, N(—$R^{17}$)CON(—$R^{18}$), $SO_2$N(—$R^{19}$) or N(—$R^{19}$)$SO_2$;

$Q^2$ is selected from $C_{1-20}$ alkylene group, $C_{3-20}$ alkenylene group and $C_{3-20}$ alkynylene group, wherein O, S or phenylene group optionally is independently inserted to the alkylene group at one or more positions;

Ar is selected from 6-18 membered aromatic carbocyclic group or 5-18 membered aromatic heterocyclic group, wherein one or more rings contained in the aromatic carbocyclic group and the aromatic heterocyclic group may include a condensed ring which is an aromatic ring, and —$CH_2$— present as a ring atom in the aromatic carbocyclic ring group and the aromatic heterocyclic group is optionally substituted with —C(O)—, and the aromatic carbocyclic ring group and the aromatic heterocyclic group are optionally substituted with one or more substituents selected from halogen atom, $C_{1-6}$ alkyl group, $C_{1-6}$ alkoxy group, $C_{1-6}$ alkylthio group, $C_{1-6}$ alkylsulfinyl group, $C_{1-6}$ alkylsulfonyl group, nitro group, cyano group, $C_{1-6}$ alkylcarbonyl group, $C_{1-6}$ alkoxycarbonyl group, carboxyl group, formyl group, —$NR^6R^7$ and —$SO_2NR^{14}R^{15}$ (wherein an alkyl group included in the $C_{1-6}$ alkyl group, $C_{1-6}$ alkoxy group, $C_{1-6}$ alkylthio group, $C_{1-6}$ alkylsulfinyl group, $C_{1-6}$ alkylsulfonyl group, $C_{1-6}$ alkylcarbonyl group and $C_{1-6}$ alkoxycarbonyl group is optionally substituted with one or more substituents selected from halogen atom, $C_{1-6}$ alkoxy group, hydroxyl group, amino group, $C_{1-6}$ alkylamino group, di($C_{1-6}$ alkyl) amino group, aryl group and carboxyl group);

$R^6$ and $R^7$ are independently selected from hydrogen atom, $C_{1-10}$ alkyl group, aryl group, $C_{1-10}$ alkylcarbonyl group, arylcarbonyl group, $C_{1-10}$ alkylsulfonyl group, arylsulfonyl group, carbamoyl group, N—($C_{1-10}$ alkyl)carbamoyl group and N,N-di($C_{1-10}$ alkyl)carbamoyl group, wherein an alkyl group included in the $C_{1-10}$ alkyl group, $C_{1-10}$ alkylcarbonyl group, $C_{1-10}$ alkylsulfonyl group, N—($C_{1-10}$ alkyl)carbamoyl group and N,N-di($C_{1-10}$ alkyl)carbamoyl group is optionally substituted with one or more substituents selected from halogen atom, $C_{1-6}$ alkoxy group, hydroxyl group, amino group, $C_{1-6}$ alkylamino group, di($C_{1-6}$ alkyl) amino group, aryl group and carboxyl group, and further an aryl group included in the aryl group, arylcarbonyl group and arylsulfonyl group is optionally substituted with one or more substituents selected from halogen atom, $C_{1-6}$ alkyl group, $C_{1-6}$ alkoxy group and carboxyl group; or $R^6$ and $R^7$, together with nitrogen atom which is bonded to $R^6$ and $R^7$, form 4-8 membered nitrogen-containing heterocycle, wherein the heterocycle is optionally substituted with one or more substituents selected from $C_{1-6}$ alkyl group, $C_{1-6}$ alkoxy group, nitro group, halogen atom, $C_{1-10}$ alkylcarbonylamino group and arylcarbonylamino group;

$R^{12}$ is hydrogen atom, $C_{1-6}$ alky group or -$Q^2$-$X^3$—Ar, wherein the alkyl group is optionally substituted with one or more substituents selected from hydroxyl group, halogen atom, $C_{1-6}$ alkoxy group, $C_{1-6}$ alkylthio group, $C_{1-6}$ alkylsulfinyl group and $C_{1-6}$ alkylsulfonyl group;

$R^{13}$ is hydrogen atom or $C_{1-6}$ alkyl group, wherein the alkyl group is optionally substituted with one or more substituents selected from hydroxyl group, halogen atom, $C_{1-6}$ alkoxy group, $C_{1-6}$ alkylthio group, $C_{1-6}$ alkylsulfinyl group and $C_{1-6}$ alkylsulfonyl group;

$R^{14}$ and $R^{15}$ are independently selected from hydrogen atom and $C_{1-6}$ alkyl group; or $R^{14}$ and $R^{15}$, together with nitrogen atom which is bonded to $R^{14}$ and $R^{15}$, form 4-8 membered nitrogen-containing heterocycle;

$R^{16}$, $R^{17}$, $R^{18}$ and $R^{19}$ are independently selected from hydrogen atom and $C_{1-6}$ alkyl group, wherein the alkyl group is optionally substituted with one or more substituents selected from hydroxyl group, halogen atom, $C_{1-6}$ alkoxy group, $C_{1-6}$ alkylthio group, $C_{1-6}$ alkylsulfinyl group and $C_{1-6}$ alkylsulfonyl group.]

In the temperature sensitive probe of the present invention, a second fluorescent unit can be used together in some cases. When the second fluorescent unit is used together, the fluorescent unit explained previously is named "the first fluorescent unit".

The second fluorescent unit should have the maximum fluorescence wavelength different from the first fluorescent unit. In the embodiment using the second fluorescent unit, when measuring temperature using the temperature sensitive probe of the present invention, temperature can be easily measured at high precision and in a short time by calculating a ratio of the fluorescence intensity from the first fluorescent unit and the fluorescence intensity from the second fluorescent unit, and correlating the ratio with a real temperature.

The first fluorescent unit and the second fluorescent unit preferably generate fluorescence of different maximum fluorescence wavelength from each other under the irradiation of the excitation light of the same wavelength. In addition, the difference in the maximum fluorescence wavelength between the first fluorescent unit and the second fluorescent unit, when measuring fluorescence intensity of the two wavelengths simultaneously, is not limited as long as the difference can be distinguished sufficiently by a measuring instrument, and is preferably 50 nm or more.

According to a preferable embodiment of the present invention, in either of the first fluorescent unit and the second fluorescent unit, the fluorescence intensity should increase depending on the increase in the temperature, in the other unit, fluorescence intensity should be unchanged or decrease depending on the increase in the temperature, and preferably should decrease.

A suitable example of the second fluorescent unit used with the first fluorescent unit represented in formula (c) has a repeat structure derived from a monomer represented by the following formula (c):

[Chem. 11]

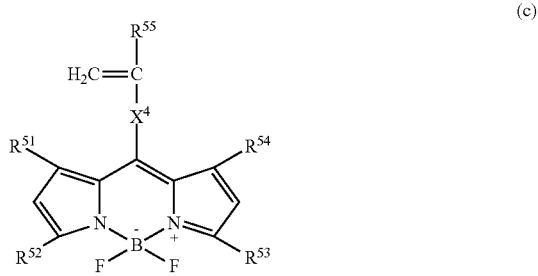

(c)

[wherein $R^{55}$ is selected from hydrogen atom and $C_{1-3}$ alkyl group;

$R^{51}$, $R^{52}$, $R^{53}$ and $R^{54}$ are independently selected from hydrogen atom and $C_{1-6}$ alkyl group;

$X^4$ is a direct bond, phenylene group, -$Q^4$-O—C(=O)— (wherein $Q^4$ is directly bonded to the borondipyrromethene skeleton), -$Q^4$-N(—$R^{61}$)—C(=O)— (wherein $Q^4$ is directly bonded to the borondipyrromethene skeleton);

$R^{61}$ is selected from hydrogen atom and $C_{1-6}$ alkyl group;

$Q^4$ is selected from $C_{1-20}$ alkylene group, phenylene group and naphthylene group, wherein the phenylene group and the naphthylene group are optionally substituted with one or more substituents selected from halogen atom, $C_{1-6}$ alkoxy group, hydroxyl group, amino group and carboxyl group]

(3) The Copolymers used as Temperature-Sensitive Probes of the Present Invention In a preferred embodiment of the present invention, the copolymers used in the present invention are those containing the structures derived from the cationic polymerization initiator represented by formula (I) on at least one of the ends of the main chain, and the subsequent repeat structures derived from the corresponding monomers represented by formula (a) and formula (b), as well as the cross-linked structure by the crosslinkers.

According to a more preferable embodiment of the present invention, a copolymer used for the present invention contains repeat units represented by formula (I'), formula (A) and formula (B) and further has a cross-linked structure generated by the crosslinking agent $M_K$.

[Chem. 12]

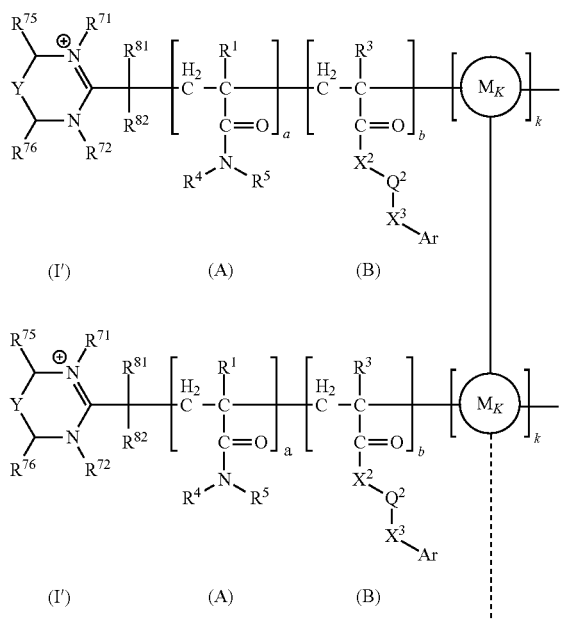

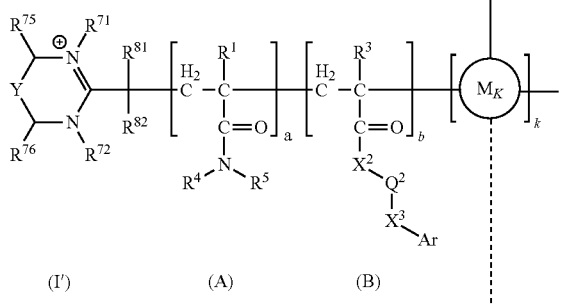

In the copolymer, "a" is 100, "b" is preferably 0.05-2. In addition, with the proviso that the structure of formula (I') is present at the terminal, the copolymer may have other repetition structures, that is, the repeat unit of formula (A) and formula (B) and the cross-linked structure generated by the crosslinking agent $M_K$ may be lined in any order. Further, the copolymer may include one kind or two kinds or more of each repeat units represented by each formula. The copolymer constitute one embodiment of the present invention as material itself.

In another preferred embodiment of the present invention, the copolymers used in the present invention are those containing the structures derived from the cationic polymerization initiator represented in formula (I) on at least one of the ends of the main chain, and the subsequent repeat structures derived from the corresponding monomers represented by formula (a), (b) and (c) as well as the cross-linked structure by the crosslinkers.

According to a more preferable embodiment of the present invention, a copolymer used for the present invention contains repeat units represented by formula (I'), formula (A), formula (B) and formula (C) and further has a cross-linked structure generated by the crosslinking agent $M_K$.

[Chem. 13]

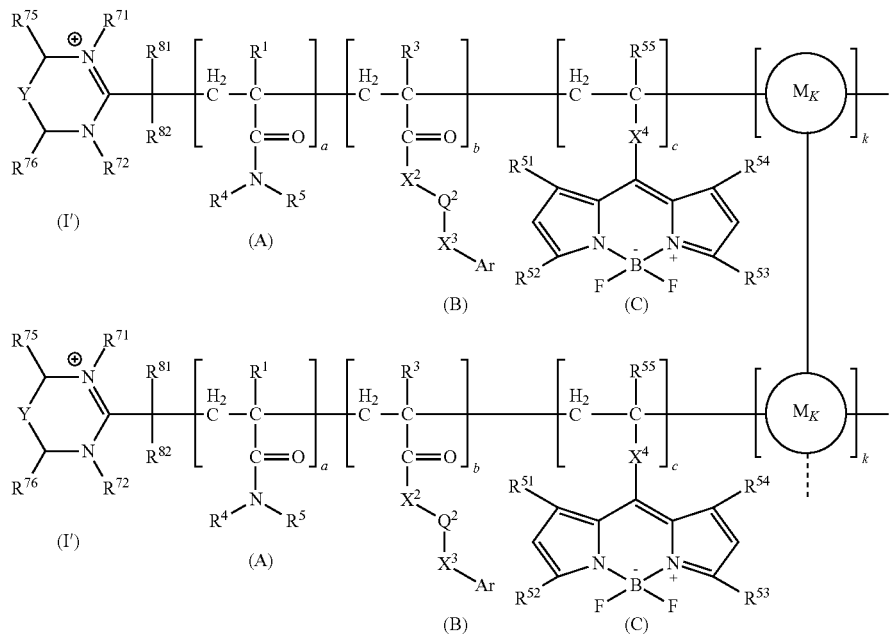

[wherein $R^{71}$, $R^{72}$, $R^{75}$, $R^{76}$, $R^{81}$, $R^{82}$ and Y, $R^1$, $R^4$ and $R^5$, and $R^3$, $X^2$, $X^3$, $Q^2$ and Ar are as already defined, and "a" and "b" are the numbers representing the ratio of the each repeat unit and larger than 0.]

[wherein $R^{71}$, $R^{72}$, $R^{75}$, $R^{76}$, $R^{81}$, $R^{82}$ and Y, $R^1$, $R^4$ and $R^5$, and $R^3$, $X^2$, $X^3$, $Q^2$ and Ar, and $R^{55}$, $X^4$, $R^{51}$, $R^{52}$, $R^{53}$ and $R^{54}$ are as already defined, and "a", "b" and "c" are the numbers representing the ratio of the each repeat unit and larger than 0.]

In the copolymer, "a" is 100, "b" is preferably 0.05-2, and "c" is preferably 0.005-1. In addition, with the proviso that the structure of formula (I') is present at the terminal, the copolymer may have other repetition structures, that is, the repeat unit of formula (A), formula (B) and formula (C) and the cross-linked structure generated by crosslinking agent $M_K$ may be lined in any order. Further, the copolymer may include one kind or two kinds or more of each repeat units represented by each formula. The copolymer constitutes one embodiment of the present invention as material itself.

In a preferred embodiment of the present invention, the copolymers contain two or more types of heat-sensitive units. There are many types of heat-sensitive units, and their temperature ranges that provide the highest heat-response differ depending on the type. In this embodiment, by combing two or more types of heat-sensitive units, the heat-response of the copolymers can be adjusted to be high in the desired temperature range. In a more preferred embodiment of the present invention, the copolymers contain two or more types of heat-sensitive units represented by the formula (a). Additionally, in one embodiment, two types of heat-sensitive units are used. For example, for the measurement around 35° C., the typical temperature to cultivate animal cell lines, the use of a combination of N-n-propylacrylamide (NNPAM) and N-isopropylacrylamide (NIPAM) is preferred. On the other hand, in the case where measurements at 25° C. or lower is required, for the purpose of such as monitoring fermentation of microorganisms such as yeast, the use of a combination of N-tert-butylacrylamide (NT-BAM) and NNPAM is preferred.

In formula (A), "a" represents either the total (number) of the heat-sensitive units as a whole, or in the case where two types or more heat-sensitive units are used, the sum of the ratio of the repeat units of all the heat-sensitive units.

According to a preferable embodiment of the present invention, Ar in the above-mentioned copolymer is an aromatic carbocyclic group or an aromatic heterocyclic group selected from the groups represented in the following formula:

[Chem. 14]

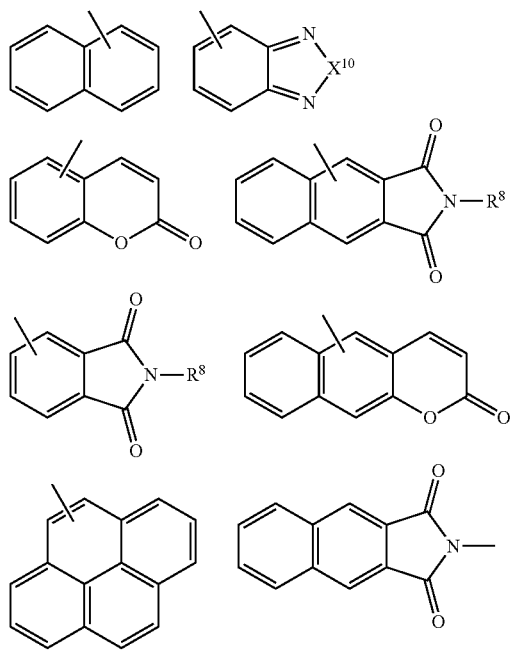

-continued

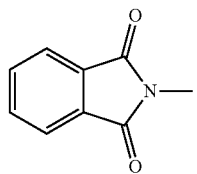

wherein the groups are optionally substituted at the ring with one or more substituents selected from halogen atom, $C_{1-6}$ alkyl group, $C_{1-6}$ alkoxy group, $C_{1-6}$ alkylthio group, $C_{1-6}$ alkylsulfinyl group, $C_{1-6}$ alkylsulfonyl group, nitro group, cyano group, $C_{1-6}$ alkylcarbonyl group, $C_{1-6}$ alkoxycarbonyl group, carboxyl group, formyl group, —$NR^6R^7$ and —$SO_2NR^{14}R^{15}$ (wherein an alkyl group included in the $C_{1-6}$ alkyl group, $C_{1-6}$ alkoxy group, $C_{1-6}$ alkylthio group, $C_{1-6}$ alkylsulfinyl group, $C_{1-6}$ alkylsulfonyl group, $C_{1-6}$ alkylcarbonyl group and $C_{1-6}$ alkoxycarbonyl group is optionally substituted with one or more substituents selected from halogen atom, $C_{1-6}$ alkoxy group, hydroxyl group, amino group, $C_{1-6}$ alkylamino group, di($C_{1-6}$ alkyl)amino group, aryl group and carboxyl group);

$X^{10}$ is selected from O, S or Se;

$R^8$ is selected from hydrogen atom, $C_{1-10}$ alkyl group and aryl group, wherein the alkyl group is optionally substituted with one or more substituents selected from halogen atom, $C_{1-6}$ alkoxy group, hydroxyl group, amino group, $C_{1-6}$ alkylamino group, di($C_{1-6}$ alkyl)amino group, aryl group and carboxyl group, and further the aryl is optionally substituted with one or more substituents selected from halogen atom, $C_{1-6}$ alkyl group, $C_{1-6}$ alkoxy group and carboxyl group.

According to a more preferable embodiment of the present invention, Ar is an aromatic carbocyclic group or an aromatic heterocyclic group selected from the groups represented by the following formula:

[Chem. 15]

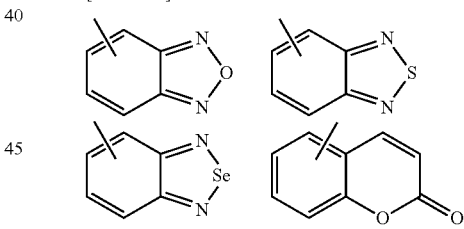

wherein the groups are optionally substituted at the ring with one or more substituents selected from halogen atom, $C_{1-6}$ alkyl group, $C_{1-6}$ alkoxy group, $C_{1-6}$ alkylthio group, $C_{1-6}$ alkylsulfinyl group, $C_{1-6}$ alkylsulfonyl group, nitro group, $C_{1-6}$ alkylcarbonylamino group, arylcarbonylamino group, cyano group, formyl group, $C_{1-6}$ alkylcarbonyl group, $C_{1-6}$ alkoxycarbonyl group, carboxyl group and —$SO_2NR^{14}R^{15}$.

In the present invention, $R^1$, $R^2$, $R^3$ and $R^{55}$ are preferably selected from hydrogen atom and methyl group.

—$NR^4R^5$ in formula (a) and formula (A) is not limited in particular, but $R^4$ may be hydrogen atom and, $R^5$ may be $C_{2-10}$ alkyl group, for example. Further, when $R^4$ and $R^5$, together with nitrogen atom which is bonded to $R^4$ and $R^5$, form 4-8 membered nitrogen-containing heterocycle, $R^4$ and $R^5$ may form, for example, pyrrolidine ring, piperidine ring, homopiperidine ring, piperazine ring, homopiperazine ring, morpholine ring, thiomorpholine ring and the like.

As for —$X^2$-$Q^2$- in formula (b) and formula (B), preferably $X^2$ is O, NH or N ($C_{1-6}$ alkyl), and $Q^2$ is $C_{2-10}$ alkylene group.

—Ar in formula (b) and formula (B) are preferably groups selected from (V)-(XII) in the following formula:

[Chem. 16]

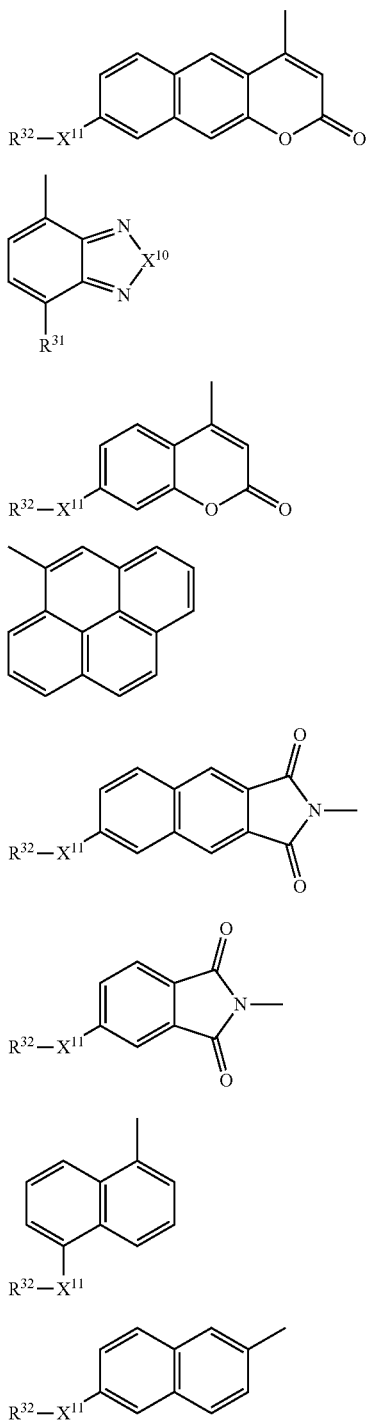

[wherein $R^{31}$ is selected from hydrogen atom, halogen atom, nitro group, cyano group and —$SO_2NR^{14}R^{15}$; $R^{32}$ is $C_{1-6}$ alkyl group; $X^{11}$ is N—$R^{33}$, O or S; $R^{33}$ is hydrogen atom or $C_{1-6}$ alkyl group; and $X^{10}$, $R^{14}$ and $R^{15}$ are as already defined.]

Preferable $X^3$ in formula (V) includes, for example, a direct bond, CON(—$R^{16}$), N(—$R^{16}$)CO, $SO_2N$(—$R^{19}$) or N(—$R^{19}$)$SO_2$.

Preferable $X^3$ in formula (VI) includes, for example, N—$R^{13}$ (wherein preferable $R^{13}$ includes $C_{1-3}$ alkyl group such as methyl group) or S.

Preferable $X^3$ in formula (VII) includes, for example, a direct bond, CON(—$R^{16}$), N(—$R^{16}$)CO, $SO_2N$(—$R^{19}$) or N(—$R^{19}$)$SO_2$.

Preferable $X^3$ in formula (VIII) includes, for example, a direct bond, CON(—$R^{16}$), N(—$R^{16}$)CO, $SO_2N$(—$R^{19}$) or N(—$R^{19}$)$SO_2$.

Preferable $X^3$ in formula (IX) includes, for example, a direct bond.

Preferable $X^3$ in formula (X) includes, for example, a direct bond.

Preferable $X^3$ in formula (XI) includes, for example, CO, $SO_2$, $SO_2N$(—$R^{19}$) or CON(—$R^{16}$) (wherein the sulfur atom and the carbon atom in said $SO_2N$(—$R^{19}$) and CON(—$R^{16}$), are bonded to Ar).

Preferable $X^3$ in formula (XII) includes, for example, CO, $SO_2$, $SO_2N$(—$R^{19}$) or CON(—$R^{16}$) (wherein the sulfur atom and the carbon atom in said $SO_2N$(—$R^{19}$) and CON(—$R^{16}$), are bonded to Ar).

In the present invention, —$X^3$—Ar functions as an environment-responsive fluorophore, for example, in the case where either formulas (V) or (VII) is used as a fluorophore, a temperature sensor of which fluorescence intensity lowers relative to temperature rise, and in the case where one of the formulas (VI) or (VIII)-(XII) is used as a fluorophore, a temperature sensors of which fluorescence intensity increases relative to temperature rise, are obtained.

$R^{51}$, $R^{52}$, $R^{53}$ and $R^{54}$ in formula (c) and formula (C) preferably are independently selected from hydrogen atom and methyl group.

Preferable $X^4$ in formula (c) and formula (C) is, for example, a direct bond, phenylene group, -$Q^4$-O—C(=O)— (wherein $Q^4$ is directly bonded to the borondipyrromethene skeleton) or -$Q^4$-NH—C(=O)— (wherein $Q^4$ is directly bonded to the borondipyrromethene skeleton).

$Q^4$ in formula (c) and formula (C) is preferably phenylene group.

According to a particularly preferable embodiment of the present invention, $R^1$ is selected from hydrogen atom, methyl group and ethyl group; $R^4$ is selected from n-propyl group, isopropyl group and t-butyl group; $R^5$ is hydrogen atom; $R^3$ is selected from hydrogen atom and $C_{1-3}$ alkyl group; $X^2$ is O or N—$R^{12}$; $X^3$ is a direct bond, O, N(—$R^{13}$), CON(—$R^{16}$) N(—$R^{16}$)CO or N(—$R^{17}$)CON(—$R^{18}$); $Q^2$ is selected from $C_{1-20}$ alkylene group, $C_{3-20}$ alkenylene group or $C_{3-20}$ alkynylene group, wherein O, S or phenylene group may be independently inserted at one or more positions in the alkylene group; the Ar is aromatic carbocyclic group or aromatic heterocyclic group selected from the groups represented by the following formula:

[Chem. 17]

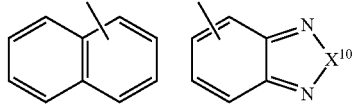

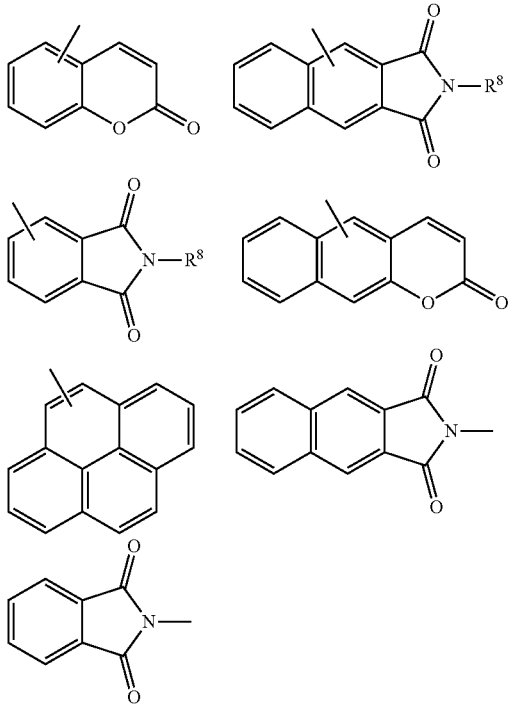

wherein these groups are substituted at the ring with one or more substituents selected from halogen atom, $C_{1-6}$ alkoxy group, nitro group, cyano group, —$NR^6R^7$ and —$SO_2NR^{14}R^{15}$, and optionally substituted with $C_{1-6}$ alkyl group; $X^{10}$ is selected from O, S or Se; $R^8$ is selected from hydrogen atom, $C_{1-10}$ alkyl group and aryl group; $R^6$ and $R^7$ are independently selected from hydrogen atom, $C_{1-10}$ alkyl group, aryl group, $C_{1-10}$ alkylcarbonyl group, arylcarbonyl group, $C_{1-10}$ alkylsulfonyl group, arylsulfonyl group and carbamoyl group; or $R^6$ and $R^7$, together with nitrogen atom which is bonded to $R^6$ and $R^7$, form 5-7 membered nitrogen-containing heterocycle, wherein the heterocycle is optionally substituted with one or more substituents selected from $C_{1-6}$ alkyl group, $C_{1-6}$ alkoxy group, nitro group and halogen atom; $R^{12}$ is hydrogen atom, $C_{1-6}$ alkyl group or -$Q^2$-$X^3$— Ar, wherein the alkyl group is optionally substituted with one or more substituents selected from hydroxyl group and halogen atom; $R^{13}$ is hydrogen atom or $C_{1-6}$ alkyl group, wherein the alkyl is optionally substituted with one or more substituents selected from hydroxyl group and halogen atom; $R^{14}$ and $R^{15}$ are independently selected from hydrogen atom and $C_{1-6}$ alkyl group; or $R^{14}$ and $R^{15}$, together with nitrogen atom which is bonded to $R^{14}$ and $R^{15}$, form a 5-7 membered nitrogen-containing heterocycle; $R^{16}$, $R^{17}$ and $R^{18}$ are independently selected from hydrogen atom and $C_{1-6}$ alkyl group, wherein the alkyl group is optionally substituted with one or more substituents selected from hydroxyl group and halogen atom; $R^{51}$, $R^{52}$, $R^{53}$, $R^{54}$ and $R^{55}$ are independently selected from hydrogen atom and methyl group; and $X^4$ is a direct bond, phenylene group, -$Q^4$-O—C(=O)— (wherein $Q^4$ is directly bonded to the borondipyrromethene skeleton) or -$Q^4$-NH—C(=O)— (wherein $Q^4$ is directly bonded to the borondipyrromethene skeleton), wherein $Q^4$ is phenylene group.

"a", "b" and "c" in formula (A), formula (B) and formula (C) are the numbers representing the ratio of repetition number of each repeat unit of the formulas and larger than 0, and, though not limited, for example, when "a" is defined as 100, "b" is 0.01-10, specifically 0.02-5, preferably 0.05-2, and more preferably 0.1-1.5. "c" is 0.001-5, specifically 0.002-2, preferably 0.005-1, and more preferably 0.01-1. b/c representing the ratio of "b" to "c" is, though not limited in particular, preferably 0.1-30, more preferably 1-20, and further preferably 3-10. "a" is a total number of heat-sensitive units as mentioned above, and the ratio of the number of the heat-sensitive units when using two types of heat-sensitive units is, for example, defined as p:(a-p) using a number "p". In addition, the size of copolymer of the present invention is, though not limited in particular, for example, 1-100000 nm, preferably 1-10000 nm, and more preferably 1-1000 nm.

The copolymer of the present invention responds to the surrounding temperature change very quickly, with its structural change occurring in a few milliseconds. That is, the temperature-sensitive probe of the present invention responds to intracellular temperature changes rapidly and change the fluorescence intensity, therefore, when visualizing intracellular temperature distribution using a microscope and the like, the intracellular temperature of each micro area within the cell can be quantified by the ratio of fluorescence intensity.

In order to measure the temperature without being affected by the pH or salt concentration of the solution containing the copolymer of the present invention, a cationic functional group belonging to the copolymer preferably remains ionic in a wide pH range. However, in terms of the use for measuring intracellular temperature alone, the range of pH inside the cells is 2-9, and in typical animal, plant, and microorganism cells under normal condition, it is about 4-8.

(4) Measuring Method

The change in fluorescence intensity of the copolymer used in the present invention due to its heat-sensitive response can be measured by conventional fluorescence intensity measuring methods. The excitation wavelength during the measurement and the fluorescence wavelength measured are not limited, however for example, the maximum or its proximal excitation wavelength of excitation spectra of the measurement sample can be used. The fluorescence wavelengths to be measured are also not limited, however for example, the maximum or its proximal fluorescence wavelength of the fluorescence spectra of the measurement sample can be used.

In the present invention, measuring the fluorescence intensity of two independent fluorescence wavelengths and obtaining their ratio, and converting the fluorescence intensity ratio to the temperature, is another viable method to take. With this method, it is possible to exclude the possibility that fluorescence intensity emitted from the copolymer is originated from the copolymer concentration within a micro area or excitation laser intensity, and to attain one-to-one correspondence of the temperature and the fluorescence intensity ratio obtained from experiment. With this, it is possible to compare not only the temperature within an identical cell but also an intracellular temperature of another cell under the same conditions. For example, by measuring the temperature difference of individual cells in a group of yeast, it is possible to grasp the physiological state of each yeast cell.

The calculation methods for fluorescence intensity ratio are not limited, and the ratio can be calculated from the fluorescence intensities of two ranges that include different wavelengths. For example, if one region is set to a wavelength range of about 20 nm that includes the wavelength showing the maximum intensity of the fluorescence emitted from the first fluorescent unit, wherein the integral value of fluorescence intensity is S1, and the other region is set to a wavelength range of about 20 nm that includes the wavelength showing maximum intensity of the fluorescence emitted from the second fluorescent unit, wherein the integral value of fluorescence intensity is S2, the fluorescence intensity ratio can be S1/S2. Furthermore, the width of the region of S1 and S2 can either be the same or different.

For example, if the fluorescence intensity shows a value sufficient to ignore the noise, then S1 involves a wavelength range of 20 nm width, while S2 can involve a wavelength range of 1 nm width. The selection criteria of wavelength also are not limited in particular, however, considering the fluorescence intensity obtained, it is preferable to select a wavelength in the vicinity of the wavelength at which the maximum fluorescence intensity is attained, when the excitation spectra of a monomer (for example, a fluorescent monomer shown in formula (b) or (c)) which gives each fluorescent unit contained in the temperature-sensitive probe are measured at normal temperature (around 25° C.) in either water or a polar solvent similar to water.

When converting the fluorescence intensity ratio obtained from experiments to temperature, it is possible to use a self-made calibration curve. Specifically, there are no limits for the use of calibration curves measured under any specific conditions, however for example, a curve that plots the fluorescence intensity changes caused by heat-sensitive response of the copolymer in a potassium chloride solution that mimics inside a cell, a curve that plots fluorescence intensity changes caused by heat-sensitive response of a copolymer introduced into cell population and placed in fluorometer, or a curve that plots average values of the fluorescence intensity changes caused by heat-sensitive response of multiple cells in which copolymers are introduced inside the cells that are placed under a fluorescence microscope, can be used. More specifically, when using a cell population to which a copolymer is introduced, testing the heat-sensitive response, and plotting the fluorescence intensity changes, a method for measuring the fluorescence intensity can be adopted, wherein the cells are maintained at a specific temperature for a certain period of time held under the conditions in which cells do not make aggressive metabolic activities, for example, by suspending the cells in water or a buffer not containing anabolic compounds, and the extra-cellular and intra-cellular temperature are considered to be equilibrated.

In addition, the fluorescence lifetime can be used as an indicator of the change of the copolymer used in the present invention due to their heat-sensitive response. The change can be measured by conventional methods for fluorescence lifetime measurements. The excitation wavelengths in the measurement are not limited in particular, however for example, the maximum or its proximal excitation wavelength of the exaction spectra of the measurement sample can be used. From the fluorescence decay curve obtained by the experiment, depending on the conditions of the sample, use of conventional analytical methods such as one-component or two-component approximation provides the values of fluorescence lifetime.

The fluorescence lifetime change due to heat-sensitive response of the copolymer used in the present invention can be measured by general fluorescence lifetime measurement methods such as single-photon counting method, phase modulation method, pulse sampling method, excitation probe method and the like. Among them, the single-photon measurement method is a method for measuring the fluorescence lifetime by using the fact that the emission intensity distribution along the time axis is related to the emission probability of a single photon, and determination of the fluorescence lifetime is conducted in the following way: First, excite a fluorophore with a very short (pulse) light of 50 ps-1 ns, and then measure the time of light emission; the histogram obtained by repeating the excitation for multiple times, is approximated with sum of exponential functions as a fluorescence decay curve. The measurement of fluorescence lifetime by a single-photon counting method can be conducted using a commercial time-correlated single-photon counting fluorescence lifetime measurement equipment and attached measurement/analysis programs.

(5) Kit

In order to embody the methods explained above, the necessary reagents and the like can be assembled as a kit. Therefore, in another embodiment of the present invention, a kit for measuring the temperature using the above methods is provided, wherein the kit is composed of the temperature-sensitive probe or the copolymer of the present invention. This reagent kit for temperature measurement can be favorably used for measuring temperature in micro area, in particular for measuring the intracellular temperature. The reagent kit can be used in the research fields of medical, biological, and bioengineering, as well as diagnoses and treatments in medical fields.

(6) Use of the Method and Kit of the Present Invention

The method and kit of the present invention can be applied to various research and development fields. For example, in the field of bioengineering, for microbial fermentation production of useful substances, it is expected to streamline the optimization of fermentation conditions by adding another analytical parameter, an intracellular temperature, which has been difficult to measure correctly.

The method and kit of the present invention can be applied to various medical usages. For example, by using the temperature-sensitive probe against a part of the tissue of patients, it is possible to differentiate cancer cells that are said to have high heat production from normal cells. It can be further applied to develop a more effective thermotherapy. Alternatively, introducing the temperature-sensitive probe of the present invention to brown adipose cells that have high heat production, and by measuring the temperature change in response to the addition of various materials to the cell, it is possible to screen materials that activate brown adipose cells.

The method and kit of the present invention can be applied for elucidating various physiological phenomena. For example, by studying the correlation between intracellular temperature and TRP channel, which is a receptor that senses the temperature outside a living body and causes biological reactions, activation of TRP channels different from previous approaches can be considered. Also, studying an intracellular temperature distribution and its correlation with biological reactions that occur inside or outside the cell enables studying the effect of local temperature distributions on biological reactions, as well as controlling the cell by local heating using an infrared laser and the like.

The temperature measurement method and cell delivery method of the temperature-sensitive probe according to the present invention can be conducted both in vitro and in vivo. In one embodiment, these methods are conducted in vitro.

6. Summary

As mentioned above, the present invention provides the following inventions.
(1) An intracellular delivery vehicle, of which surface is covered by a positive charge.
(2) The intracellular delivery vehicle according to (1), comprising the chemical structure shown in FIG. 13:
(3) A method for producing an intracellular delivery vehicle, of which surface is covered by a positive charge, characterized by performing a radical polymerization reaction involving a cationic polymerization initiator, a monomer comprising a carbon-carbon double bond, and a crosslinker.
(4) A compound having a chemical structure represented by General formula (I):

[Chem. 19]

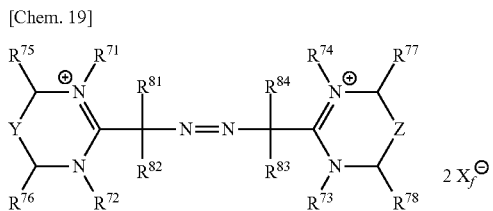

[wherein
Y represents a single bond or $CR^{85}$,
Z represents a single bond or $CR^{86}$,
$R^{72}$, $R^{73}$, $R^{75}$, $R^{76}$, $R^{77}$, $R^{78}$, $R^{85}$ and $R^{86}$ are each independently selected from the group consisting of hydrogen atom, $C_{1-6}$ alkyl group, $C_{1-6}$ alkoxy group, $C_{1-6}$ alkylcarbonyl group, phenyl group and hydroxyl group, wherein said $C_{1-6}$ alkyl group, $C_{1-6}$ alkoxy group, $C_{1-6}$ alkylcarbonyl group and phenyl group are optionally substituted with 1 or 2 substituents selected from the group consisting of $C_{1-6}$ alkyl group, $C_{1-6}$ alkoxy group, $C_{1-6}$ alkylcarbonyl group, phenyl group and hydroxyl group,
$R^{72}$ and $R^{73}$ optionally each independently represent adamanthyl group or $C_{1-6}$ alkyl group substituted with $Si(OCH_3)_2(CH_3)$, or $R^{75}$ and $R^{76}$ or $R^{77}$ and $R^{78}$ together optionally form $-(CH_2)_{3-5}-$,
$R^{81}$, $R^{82}$, $R^{83}$ and $R^{84}$ are a substituent selected from the group consisting of $C_{1-4}$ alkyl group, $C_{1-4}$ alkylcarbonyl group and $C_{1-3}$ alkoxy group, wherein the $C_{1-4}$ alkyl is optionally substituted with one $C_{1-3}$ alkoxy group; and
$R^{71}$ and $R^{74}$ each independently are $C_{1-3}$ alkyl group, and $X_f^-$ is counter anion.]
(5) The compound according to (4), wherein said Y and Z represent single bond.
(6) The compound according to (4) or (5), wherein said $R^{81}$, $R^{82}$, $R^{83}$, and $R^{84}$ are each independently selected from the group consisting of methyl group, ethyl group, methylcarbonyl group, isobutyl group, and 2-methyl-2-methoxypropyl group.
(7) The compound according to any one of (4) to (6), wherein said $R^{71}$ and $R^{74}$ are a methyl group.
(8) The compound according to any one of (4) to (7), wherein said $R^{72}$ and $R^{73}$, said $R^{75}$ and $R^{77}$, said $R^{76}$ and $R^{78}$, said $R^{81}$ and $R^{84}$, said $R^{82}$ and $R^{83}$, and said $R^{71}$ and $R^{74}$, each represent an identical substituent, and said Y and Z represent an identical substituent or a single bond.
(9) The compound according to (4), wherein said $R^{71}$, $R^{72}$, $R^{73}$, $R^{74}$, $R^{81}$, $R^{82}$, $R^{83}$, and $R^{84}$ are a methyl group, and said $R^{75}$, $R^{76}$, $R^{77}$ and $R^{78}$ are a hydrogen atom, and said Y and Z are a single bond.
(10) A cationic polymerization initiator, comprising the compound according to any one of (4) to (9).
(11) A method for producing an intracellular delivery vehicle, comprising performing radical polymerization reaction involving the cationic radical initiator according to (10), a monomer comprising carbon-carbon double bonds, and a crosslinker.
(12) An intracellular delivery vehicle, obtained by the production method according to (11).
(13) An intracellular delivery complex, obtained by loading a component or compound desired to be delivered inside a cell into the intracellular delivery vehicle according to (1).
(14) A method for producing an intracellular delivery complex, comprising loading a component or compound desired to be delivered inside a cell into the intracellular delivery vehicle according to (1).
(15) The intracellular delivery complex according to (13), wherein said component or compound desired to be delivered inside a cell is covalently bonded to the intracellular delivery vehicle.
(16) The intracellular delivery complex according to (13) or (15), wherein the compound is a heat-sensitive unit which changes its character in response to temperature, and a fluorescent unit which changes fluorescence intensity or lifetime in relation to the character change of the heat-sensitive unit.
(17) A copolymer, comprising a structure derived from a cationic polymerization initiator represented in formula (I') on at least one of the ends of a main chain, subsequent repeat structures each derived from the corresponding monomers represented by formula (a) and formula (b), and a cross-linked structure derived from a crosslinker.
(18) A copolymer, comprising repeat units represented by formula (I'), formula (A) and formula (B), and a cross-linked structure derived from a crosslinker.

(19) A copolymer, comprising a structure derived from a cationic polymerization initiator represented by formula (I') on at least one end of the main chain, subsequent repeat structures each derived from a monomer represented by formula (a), a monomer represented by formula (b), and a monomer represented by formula (c), and a cross-linked structure derived from a crosslinker.
(20) A copolymer, comprising repeat units represented by formula (I'), formula (A), formula (B) and formula (C) and a cross-linked structure derived from a crosslinker.
(21) A temperature-sensitive probe, comprising either the intracellular delivery complex according to (16), or the copolymer according to any one of the (17) to (20).
(22) A method for measuring intracellular temperature, comprising the steps of:
(a) introducing the temperature-sensitive probe according to (21) into a cell; and
(b) measuring fluorescence intensity or fluorescence lifetime under irradiation of excitation light.
(23) A kit for measuring intracellular temperature, comprising the intracellular delivery complex according to (16), the copolymer according to any one of (17) to (20), or the temperature-sensitive probe according to (21).
(24) A method for producing a linear polymer at least one end of which is positively charged, comprising conducting a radical polymerization reaction using the cationic polymerization initiator according to (10) and a monomer comprising a carbon-carbon double bond.
(25) A linear polymer at least one end of which is positively charged, comprising a structure derived from a cationic polymerization initiator represented by formula (I') on at least one end of the main chain, and subsequent repeat structures derived from a monomer comprising a carbon-carbon double bond.
(26) A linear polymer at least one end of which is positively charged, obtained by the production method according to (24).
(27) A complex, comprising a linear polymer at least one end of which is positively charged, and negatively charged ink particles.

EXAMPLES

The present invention is illustrated in further detail by the examples that follow, however is not limited to these examples.
The reagents and data measurements
α,α'-azobisisobutyronitrile (AIBN), the raw material for the synthesis of the cationic polymerization initiators, was purified by recrystallization from methanol, and the heat-sensitive unit N-isopropylacrylamide (NIPAM) by recrystallization from n-hexane. Other reagents were purchased and used without further purification.
$^1$H-NMR spectra were acquired on BRUKER AVANCE 400 spectrometer (400 MHz) and the chemical shirts were reported as ppm. The number-average molecular weight and the weight-average molecular weight were calculated using the calibration curve obtained from polystyrene standard using JACSO GPC system (JASCO PU-2080 pump, JASCO RI-2031 differential refractometer, JASCO CO-2060 column oven, Shodex GPC KD-806M column). Silica gel chromatography was conducted using silica gel 60N (40-50 μm) by Kantokagaku. Absorbance was measured using JASCO V-650 UV-VIS spectrophotometer. IR was measured using SHIMADZU FTIR-8300.

For mass spectral analyses, either JMS-700 or Brucker micrOTOF II (ESI) was used. The gel particle diameters were measured using Zetasizer Nano ZS (Malvern) based on dynamic light scattering (DLS).

Example A-1: Synthesis of the Cationic Polymerization Initiator

[Chem. 20]

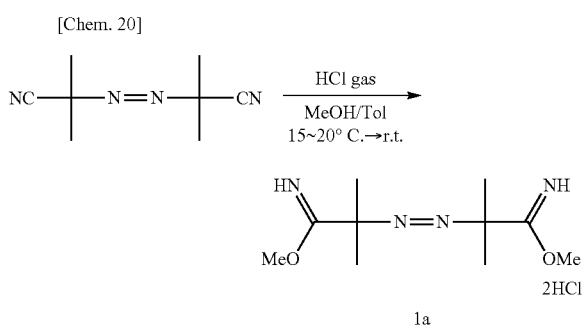 [SMILES: CC(C)(C#N)N=NC(C)(C)C#N ; COC(=N)C(C)(C)N=NC(C)(C)C(=N)OC]

α,α'-azobisisobutyronitrile (AIBN) (20.1 g, 0.12 mol) was suspended in a mixed solution of 20 mL of methanol (MeOH) and 200 mL of toluene (Tol). The solution was passed through with hydrogen chloride (HCl) gas generated by drop-wise addition of conc. sulfuric acid (260 mL) to sodium chloride (NaCl) (200 g) and stirred for 5 hours at room temperature. The precipitated solid was filtered, washed with toluene (Tol), and vacuum-dried to obtain compound 1a as white solid (28.3 g, yield 77%).
The $^1$H NMR (400 MHz, MeOD-d$_4$) of compound 1a is as follows.
δ 3.35 (s, 6H), 1.57 (s, 12H)
The results of mass spectrometry of compound 1a are as follows.
HRMS (EI$^+$): calcd for [C$_5$H$_{10}$NO]$^+$, 100.0757, found, 100.0761
Also, the results of the elemental analysis of compound 1a are as follows.
Anal. Calcd for C$_{10}$H$_{22}$Cl$_2$N$_4$O$_2$: C, 39.87; H, 7.36; N, 18.60. Found: C, 39.16; H, 7.41; N, 18.25

[Chem. 21]

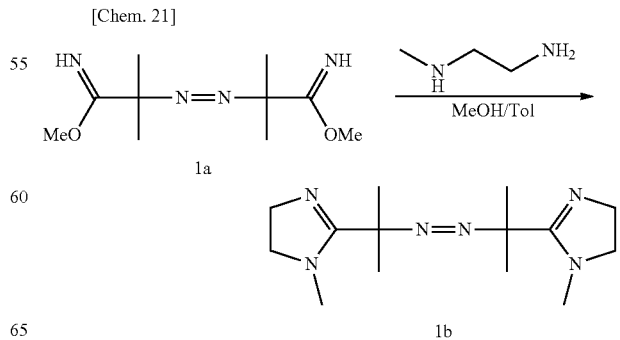

N-Methylethylenediamine (12.6 mL, 0.14 mol) was added to 60 mL of methanol (MeOH), compound 1a (15.0 g, 49.7 mmol) suspended in 100 mL of toluene (Tol)/6 mL of methanol (MeOH), was added drop-wise over 40 minutes under reduced pressure. After being stirred for 3 hours at room temperature under reduced pressure (250 Torr), the slurry was filtered. The solvent was distilled under reduced pressure until the volume of the filtrate became approximately ½, and the supernatant was removed by decantation. The supernatant was distilled under reduced pressure and vacuum-dried to obtain compound 1b as yellow solid (13.2 g, yield 95%).

The $^1$H NMR (400 MHz, MeOD-$d_4$) of compound 1b is as follows.

δ 3.66 (t, 4H, J=10.0 Hz), 3.42 (t, 4H, J=10.0 Hz), 2.75 (s, 6H), 1.47 (s, 12H).

The $^{13}$C NMR (100 MHz, MeOH-$d_4$) of compound 1b is as follows.

δ 171.0, 72.7, 55.1, 52.3, 36.0, 25.0

The results of mass spectrometry of compound 1b are as follows.

HRMS (EI$^+$): calcd for $[C_7H_{13}N_2]^+$ 125.1073; found, 125.1092

Also, the results of the elemental analysis of compound 1b are as follows.

Anal. Calcd for $C_{14}H_{26}N_6$: C, 60.40; H, 9.41; N, 30.19. Found: C, 59.79; H, 9.45, N, 29.68.

[Chem. 22]

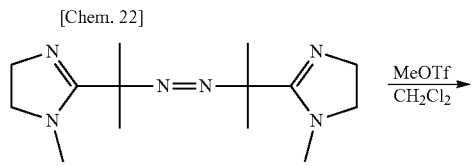

1b

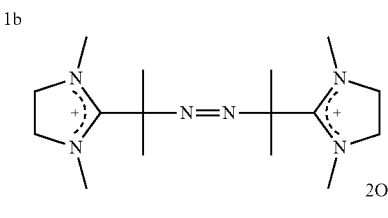

1c

Under argon environment, compound 1b (2.7 g, 9.7 mmol) was dissolved in 30 mL of dichloromethane ($CH_2Cl_2$), and methyltrifluoromethane sulfonate (MeOTf) (2.3 mL, 20.3 mmol) was added drop-wise. After being stirred for 3.5 hours at room temperature, the solvent was distilled off under reduced pressure to obtain the desired cationic polymerization initiator 1c (5.6 g, yield 95%).

The $^1$H NMR (400 MHz, MeOD-$d_4$) of compound 1c is as follows.

δ 4.00 (s, 8H), 3.24 (s, 12H), 1.73 (s, 12H)

The $^{13}$C NMR (100 MHz, MeOH-$d_4$) of compound 1c is as follows.

δ 169.0, 74.5, 53.3, 38.4, 24.7

The results of mass spectrometry of compound 1c are as follows.

HRMS (EI$^+$): calcd for $[C_7H_{13}N_2]^+$ 125.1073; found, 125.1073

Also, the results of the elemental analysis of compound 1c are as follows.

Anal. Calcd for $C_{18}H_{32}N_6O_6N_6S_2$: C, 35.64; H, 5.32; N, 13.85 Found: C, 35.37; H, 5.02; 13.59.

Example A-2: Production of Polystyrene Copolymer Using Cationic Polymerization Initiator 1c Styrene, N, N'-methylenebisacrylamide (MBAM hereafter) as a crosslinker and hexadodecyltrimethylammonium chloride (CTAC hereafter) as a surfactant were dissolved in 25 mL of water in the amounts shown in table 1, and dissolved oxygen was removed by passing through argon gas for 30 minutes. Then, cationic polymerization initiator compound 1c in the amount shown in table 1, was added and emulsion polymerization was conducted using a mechanical stirrer for 1 hour at 70° C. After being cooled to room temperature, sodium chloride was added to the reaction mixture for salting out, and the product was purified by dialysis. The yields of the polymers obtained are shown in table 1.

TABLE 1

The amounts of raw materials used, and the yield of polymer obtained in the production of polystyrene copolymers

| Compound name | Styrene | MBAM | CTAC | Compound 1c | Yield (%) |
|---|---|---|---|---|---|
| Compound 2a | 800 mM | 24 mM | 14 mM | 18 mM | 2.4 |
| Compound 2b | 800 mM | 24 mM | 14 mM | 3.6 mM | 18 |

The polymers obtained were confirmed as cationic gels, by measurements of gel particle diameters by zeta potential and DLS (polymer concentration 0.1%, 20° C.), as well as by transmission electron microscope (TEM) (polymer concentration 0.01%, measured after air-drying) that provided results shown in table 2. The result of observation of compound 2b with transmission electron microscope (TEM) is shown in FIG. 1. From these results, it became clear that the newly prepared cationic polymerization initiator compound 1c functions as a polymerization initiator and contributes to the syntheses of cationic particles. In addition, compound 2a, which was prepared with a larger amount of polymerization initiator, showed higher zeta potential compared to that of 2b, indicating that the amount of cationic charge on particle surface can be controlled by the amount of the polymerization initiator used.

TABLE 2

The particle diameters of the polymer obtained, and the effect of the amount of polymerization initiator added on the cationic charge.

| Compound name | Zeta potential (mV) | Particle size DLS (nm) | Particle size TEM (nm) |
|---|---|---|---|
| Compound 2a | 10.9 ± 0.4 | 776 ± 75 | 6.1 ± 1.7 |
| Compound 2b | −11.9 ± 1.0 | 256 ± 138 | 27.1 ± 2.7 |

Example A-3: Production of PEG Copolymer Using Cationic Polymerization Initiator 1c

[Chem. 23]

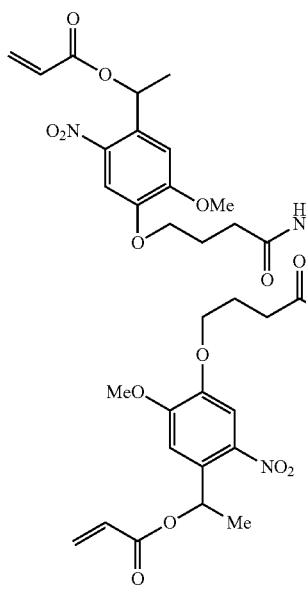
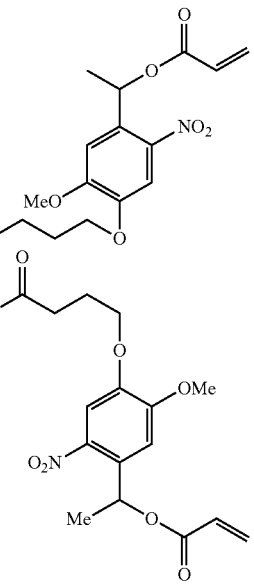

Compound 3a n = 28

PEG-photo-AM

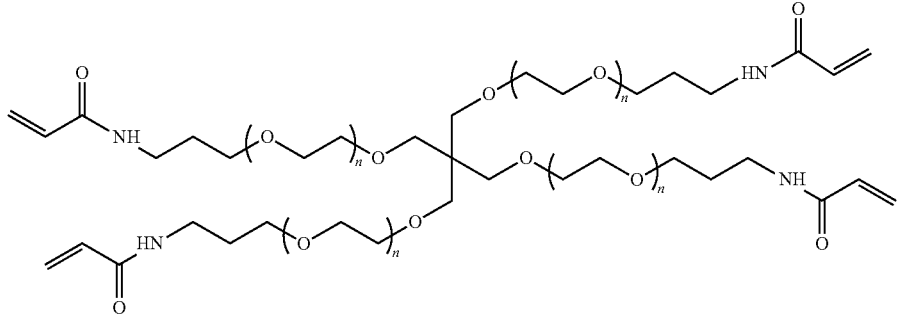

Compound 3b n = 28

PEG-AM

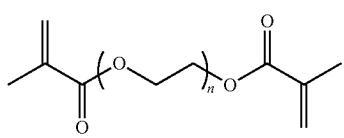

Compound 3e

PEGDMA

Copolymer 3c was obtained using compound 3a, and copolymer 3d was obtained using compound 3b. The method of their preparation is the following. Compound 3a (20 mg/mL) or compound 3b (33 mg/mL) was dissolved in water (150 μL), tetraethylmethylenediamine (17 mM) and compound 1c (50 mM) were added, and the mixture was stirred for 20 minutes. After standing for 15 minutes at room temperature, 350 μL of water or phosphate buffered saline (PBS) was added to the reaction mixture, dialysis was performed for purification using water or phosphate buffered saline (PBS) to obtain copolymers 3c and 3d.

Compound 3e (4.2 mM), p-divinylbenzene (2.8 mM), and surfactant CTAC (1.82 mM) were dissolved in 45 mL of water, and dissolved oxygen was removed by passing through argon gas for 30 minutes. To this was added 5 mL of aqueous solution of cationic polymerization initiator compound 1c (9.0 mM final concentration), and emulsion polymerization was conducted at 70° C. for 1.5 hours using a mechanical stirrer. After being cooled to room temperature, dialysis was performed for purification using phosphate buffered saline (PBS) to obtain copolymer compound 3f (yield 4.2%).

Compound 3b (33 mg/mL), fluorescein (33 μg/mL), and rhodamine B (33 μg/mL) were dissolved in water (150 μL), tetraethylmethylenediamine (17 mM) and compound 1c (50 mM) were added, and the mixture was stirred for 20 minutes. After standing for 15 minutes at room temperature, 350 μL of water or phosphate buffered saline (PBS) was added to the reaction mixture, dialysis was performed for purification using water or phosphate buffered saline (PBS) to obtain copolymer 3G (containing fluorescein) and 3h (containing rhodamine B).

Figure 2:
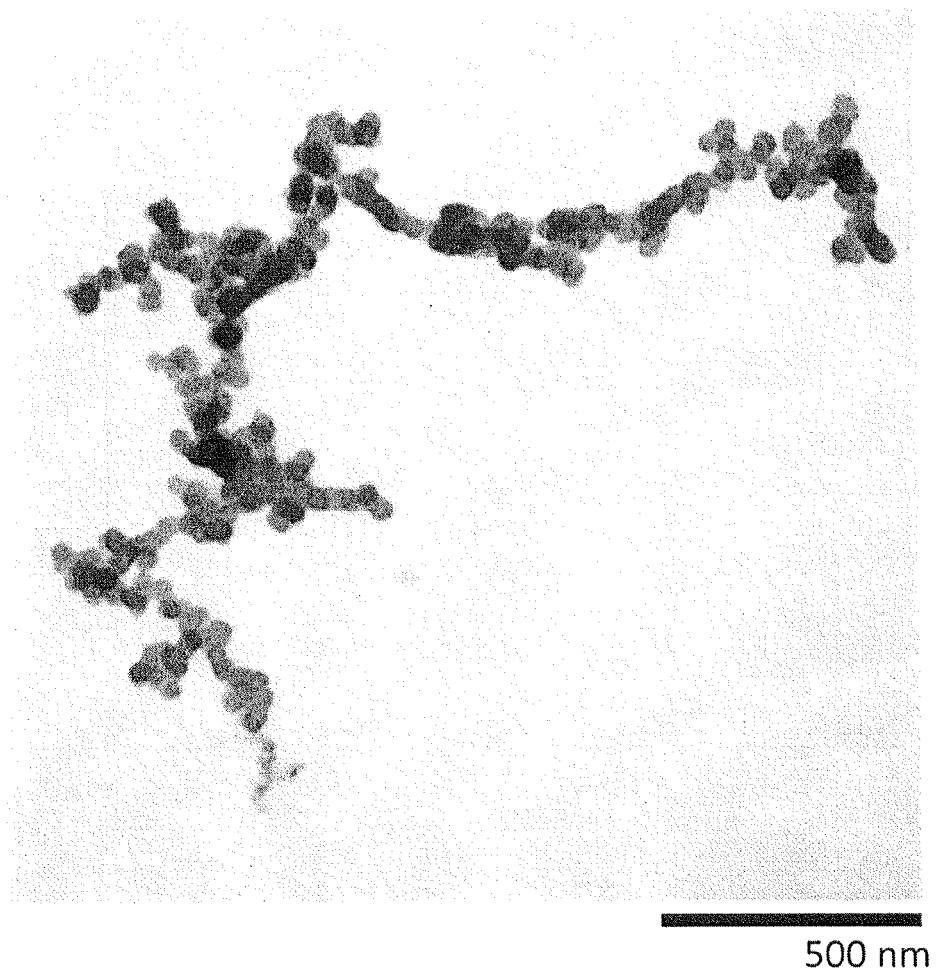
FIG. 2 An example of the result of the observation of compound 3d by TEM.

The gel particle sizes of the polymers obtained were measured (20° C.) using zeta potential and DLS, and their gel particle size measurements (taken after air-drying) were done using transmission electron microscope (TEM hereafter). As an example, the transmission electron microscope (TEM) image of compound 3d is shown in FIG. 2. The acquired results shown in table 3 confirmed that cationic gels were obtained when PEG-type monomers were used.

TABLE 3

The particle sizes and the cationic charges of the particle surface of the polymers obtained

| Compound name | Zeta potential (mV) | Particle size DLS (nm) | Particle size TEM (nm) |
|---|---|---|---|
| Compound 3c | 21.2 ± 1.3 | 4.1 ± 0.7 | 12.7 ± 2.0 |
| Compound 3d | 23.2 ± 2.9 | 4.7 ± 0.2 | 43.5 ± 4.7 |
| Compound 3f | −9.7 ± 0.5 | 233 ± 4.4 | 22.1 ± 3.9 |
| Compound 3G | 2.9 ± 0.2 | 19.3 ± 6.7 | Not measured |
| Compound 3h | 3.7 ± 0.2 | 9.3 ± 2.3 | Not measured |

Example A-4: Production of Temperature-Sensitive Copolymer Using Cationic Polymerization Initiator 1c

[Chem. 24]

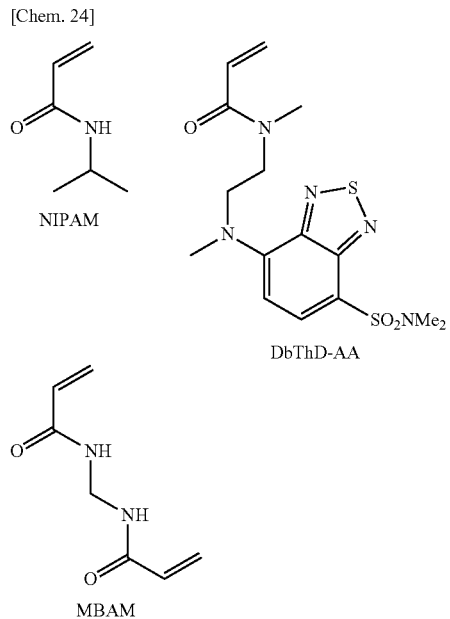

One of the monomers (fluorescent unit) necessary for the synthesis of copolymer polymerization, N-(2-{[7-(N,N-dimethylaminosulfonyl)-2,1,3-benzothiadiazol-4-yl]-(methyl)amino}ethyl)-N-methylacrylamide (DBThD-AA) was prepared according to the method described in literature A (Chemistry A European Journal, 2012, vol. 18, pages 9552-9563).

Figure 3:
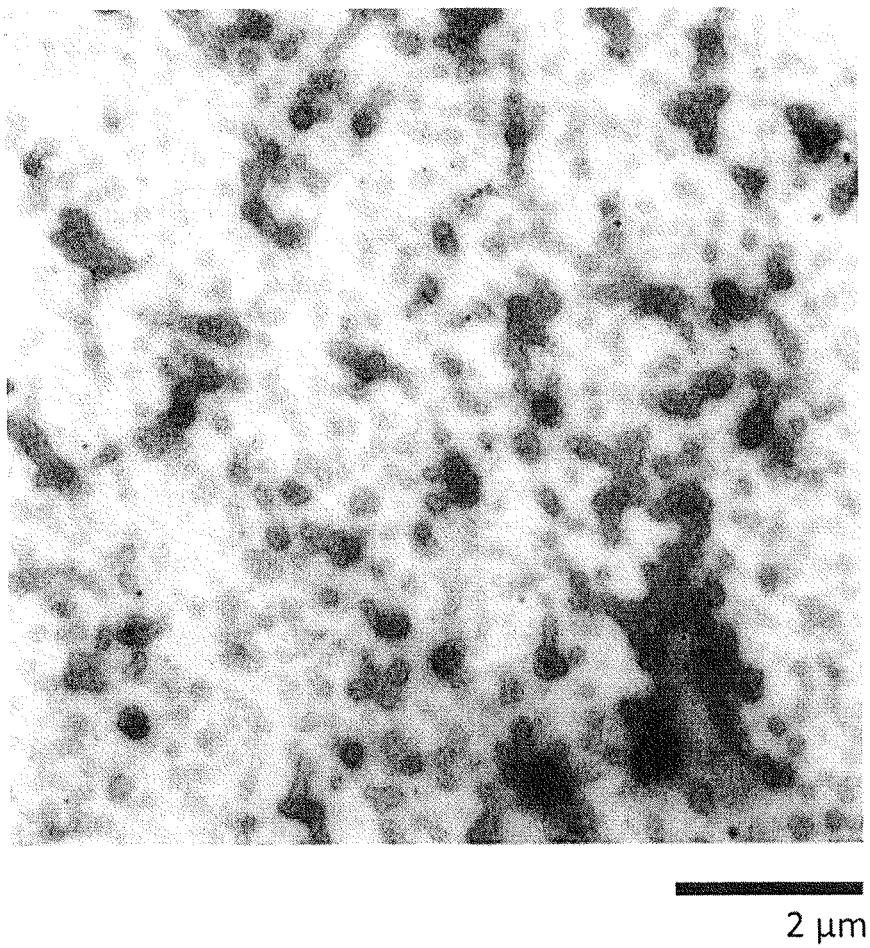
FIG. 3 An example of the result of the observation of compound EF043 by TEM.

The heat-sensitive unit N-isopropylacrylamide (NIPAM) (100 mM), crosslinker MBAM (1 mM), surfactant CTAC (1.9 mM), and fluorescent unit N-(2-{[7-(N,N-dimethylaminosulfonyl)-2,1,3-benzothiadiazol-4-yl]-(methyl)amino}ethyl)-N-methylacrylamide (DBThD-AA) (1 mM), and N,N,N',N'-tetramethylenediamine (2.9 mM) were dissolved in water (19 mL) and dissolved oxygen was removed by passing through argon gas for 30 minutes. To this was added 1 mL of aqueous solution of compound 1c (28 mM), and emulsion polymerization was conducted at 70° C. for 1 hour by using a mechanical stirrer. After being cooled to room temperature, sodium chloride was added to the reaction mixture for salting-out, dialysis was performed for purification using water to obtain 75.3 g of copolymer compound EF043 (yield 31%). The observed result using transmission electron microscope (TEM) of the gel obtained is shown in FIG. 3. The synthesis of spherical particles was clearly confirmed from these results observed.

Example B-1: Synthesis of a Novel Acrylamide-Type Cationic Unit Having Cationic Structure Identical to a Cationic Polymerization Initiator

[Chem. 25]

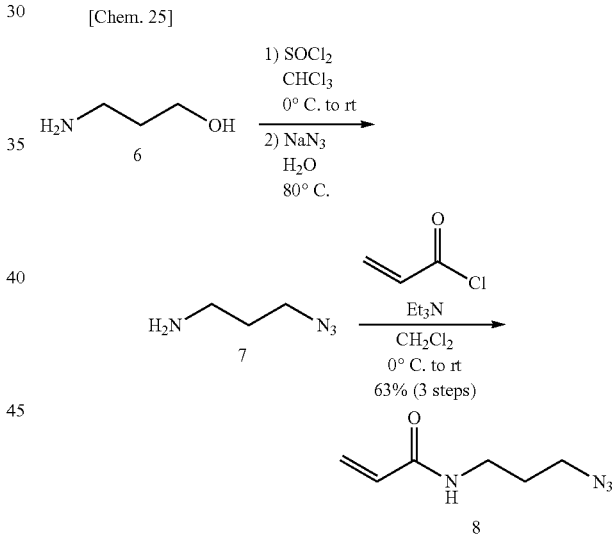

To an agitated mixture of thionylchloride (SOCl$_2$) (2.65 mL, 36.5 mmol) and trichloromethane (CHCl$_3$) (15.0 mL) was added aminoalcohol compound 6 (2.27 mL, 29.7 mmol) at 0° C. The mixture was then refluxed with heating for 3 hours until compound 6 disappeared completely. After the suspension being cooled to room temperature, it was filtered and washed well with trichloromethane (CHCl$_3$) to obtain a brown solid. To this was added sodium azide (NaN$_3$) (2.91 g, 44.7 mmol) and water (40 mL), and the mixture was heated for 24 hours at 80° C. until the brown solid reacted completely. The reaction was stopped by addition of 2 M sodium hydroxide (NaOH) and the mixture was extracted 3 times with dichloromethane (CH$_2$Cl$_2$). The extract was washed with brine, dried over anhydrous sodium sulfate, filtered, and concentrated under reduced pressure to obtain azide compound 7.

Azide compound 7 and triethylamine (Et₃N) (6.85 mL, 49.3 mmol) were dissolved in dichloromethane (CH₂Cl₂) (132 mL), and acryloyl chloride (2.69 mL, 32.9 mmol) was added at 0° C. The mixture was warmed to room temperature, and stirred for 45 minutes until azide compound 7 disappeared. The reaction was stopped by addition of water, and the mixture was extracted 3 times with dichloromethane (CH₂Cl₂). The extract was washed with brine, dried over anhydrous sodium sulfate, filtered, and concentrated under reduced pressure to obtain a crude product. Then, the crude product was purified by silica gel chromatography (Hexane/Ethyl acetate=1/1) to obtain amide compound 8 as yellow crystals (2.87 g, 18.6 mmol, yield 63%).

The IR data of compound 8 are as follows.

IR (neat, cm$^{-1}$): 3277, 2932, 2097, 1657, 1626, 1550, 1408, 1245, 985, 957, 772

The $^1$H NMR (400 MHz, CDCl₃) data of compound 8 are as follows.

δ 6.29 (dd, 1H, J=17.2, 1.2 Hz), 6.09 (dd, 1H, J=17.2, 10.0 Hz), 5.73 (brs, 1H), 5.66 (dd, 1H, J=10.0, 1.6 Hz), 3.48-3.35 (m, 4H), 1.85 (tt, 2H, J=6.8, 6.8 Hz)

The $^{13}$C NMR (100 MHz, CDCl₃) data of compound 8 are as follows.

δ 165.7, 130.7, 126.6, 49.4, 37.2, 28.7

The results of mass spectrometry of compound 8 are as follows.

HRMS (FAB⁺) calcd. for C₈H₁₃NO₂ (M+H+), 155.0933; found, 155.0936.

[Chem. 26]

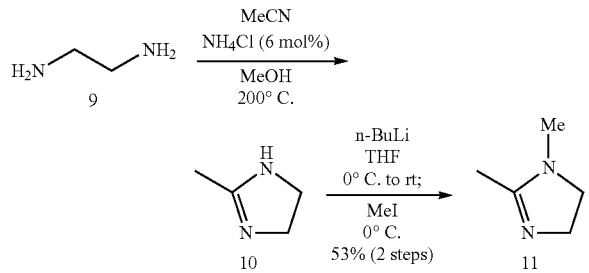

Ethylene diamine (compound 9) (5.42 mL, 81.1 mmol), acetonitrile (8.47 mL, 162 mmol), methanol (4.39 mL) and ammonium chloride (270 mg, 4.06 mmol) were added to a Paar pressure reactor and the reactor was sealed. After being heated for 4 hours at 200° C., the reaction mixture was filtered and concentrated under reduced pressure to obtain imidazoline compound 10.

Imidazoline compound 10 was dissolved in anhydrous tetrahydrofuran (THF) (243 mL), and n-butyllithium (n-BuLi) (36.7 mL, 2.65 M in n-hexane, 97.3 mmol) was added drop-wise at 0° C., and the mixture was stirred for 1 hour at room temperature. Then, methyl iodide (6.56 mL, 105 mmol) was added drop-wise at 0° C., and the mixture was stirred for 1 hour until compound 10 disappeared completely. Water was added to stop the reaction, and the mixture was extracted 3 times with dichloromethane (CH₂Cl₂). The extract was washed with brine, dried over anhydrous sodium sulfate, filtered, and concentrated under reduced pressure to obtain a crude product. Purification by distillation (54° C./27 hPa) provided dimethylimidazoilne compound 11 as colorless liquid (4.22 g, 43.0 mmol, yield 53%).

The analysis data of compound 11 is as shown in Ye, G; Henry, W. P; Chen, C; Zhou, A.; Pittman Jr., C. U. Tetrahedron Lett. 2009, 50, 2135-2139, and the R$_f$ value determined from TLC is shown as follows.

R$_f$=0.42 (hexane/n-propylamine=10/3)

[Chem. 27]

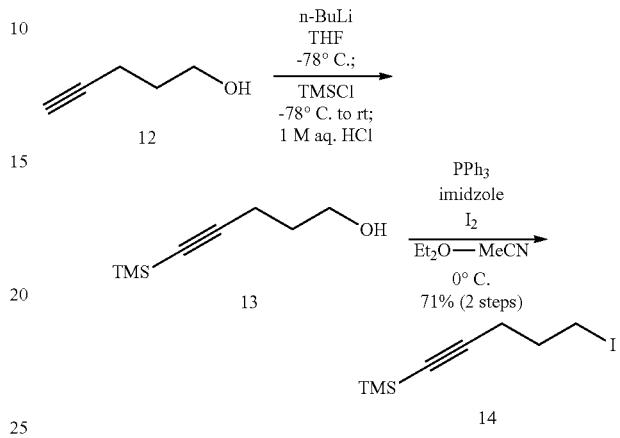

4-Pentyn-1-ol (Compound 12) (1.53 mL, 16.5 mmol) was dissolved in anhydrous tetrahydrofuran (THF) (30.0 mL), and n-butyllithium (n-BuLi) (13.6 mL, 2.66 M in n-hexane, 36.2 mmol) was added drop-wise at −78° C., and the mixture was stirred for 2 hours. Then, chlorotrimethylsilane (TMSCl) (4.80 mL, 37.9 mmol) was added drop-wise at −78° C., and the mixture was warmed to room temperature, and stirred for 10 hours to promote the reaction until compound 12 disappeared completely. 1 M hydrochloric acid (5 mL) was added to stop the reaction, and the mixture was extracted 3 times with dichloromethane (CH₂Cl₂). The extract was washed with brine, dried over anhydrous sodium sulfate, filtered, and concentrated under reduced pressure to obtain a crude product of alcohol compound 13.

To a mixture of anhydrous diethyl ether (32.1 mL) and acetonitrile (22.5 mL), compound 13, triphenylphosphine (PPh₃) (7.58 g, 28.9 mmol), imidazole (2.08 g, 30.5 mmol) were added and the mixture was stirred. The mixture was charged with iodine (8.15 g, 32.1 mmol) at 0° C., and the resulting mixture was stirred for 2 hours until compound 13 completely reacted. A saturated solution of sodium pyrosulfate was added to stop the reaction, and the mixture was extracted 3 times with diethyl ether. The extract was washed with brine, dried over anhydrous sodium sulfate, filtered, and concentrated under reduced pressure to obtain a crude product. The crude product was purified by silica gel chromatography (pentane) to obtain iodoalkyl compound 14 as colorless oil. (3.12 g, 11.6 mmol, yield 71%).

The analysis data of compound 14 is as shown in Braese, S.; Wertal, H.; Frank, D.; Vidovic, D.; de Meijere, A. Eur. J. Org. Chem. 2005, 4167-4178, and the R$_f$ value determined from TLC is shown as follows.

R$_f$=0.24 (pentane)

The IR data of compound 14 are as follows.

IR (neat, cm$^{-1}$): 2958, 2898, 2176, 1426, 1250, 1221, 901, 842, 760, 698, 638

The $^1$H NMR (400 MHz, CDCl₃) data of compound 14 are as follows.

3.29 (t, 2H, J=6.8 Hz), 2.36 (t, 2H, J=6.8 Hz), 2.00 (tt, 2H, J=6.8, 6.8 Hz), 0.15 (s, 9H)

The $^{13}$C NMR (100 MHz, CDCl$_3$) data of compound 14 are as follows.

δ 104.7, 85.7, 32.0, 20.8, 4.9, 0.1

The results of mass spectrometry of compound 14 are as follows.

HRMS (FAB$^+$ calcd. for C$_8$H$_{16}$SiI (M+H$^+$), 267.0066; found, 267.0087.

[Chem. 28]

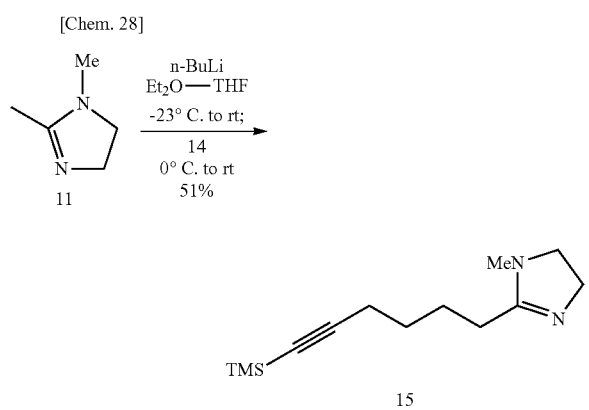

Imidazoline compound 11 (300 mg, 3.06 mmol) was dissolved in a mixture of anhydrous tetrahydrofuran (THF) (1.8 mL) and diethyl ether (2.7 mL), and n-butyllithium (n-BuLi) (2.76 mL, 1.55 M in n-hexane, 4.28 mmol) was added drop-wise at −23° C., and the mixture was warmed to room temperature and stirred for 1 hour. Then iodoalkyl compound 14 (901 mg, 3.38 mmol), dissolved in anhydrous tetrahydrofuran (THF) (3 mL), was added at 0° C. through a cannula to the mixture stirred. The mixture was warmed to room temperature, and stirred for 1 hour to promote the reaction until compound 11 disappeared completely. Water was added to stop the reaction, and the mixture was extracted 3 times with trichloromethane (CHCl$_3$). The solvent was removed under reduced pressure, and the extract was purified by silica gel chromatography (hexane/n-propylamine=5/1) to obtain compound 15 as yellow oil (370 mg, 1.57 mmol, yield 51%).

The IR data of compound 15 are as follows.

IR (neat, cm$^{-1}$): 2955, 2862, 2172, 1616, 1453, 1404, 1249, 843, 760, 640

The $^1$H NMR (400 MHz, CDCl$_3$) data of compound 15 are as follows.

δ 3.63 (t, 2H, J=9.2 Hz), 3.24 (t, 2H, J=9.2 Hz), 2.78 (s, 3H), 2.26 (t, 2H, J=7.2 Hz), 2.21 (t, 2H, J=7.6 Hz), 1.79-1.67 (m, 2H), 1.60 (tt, 2H, J=7.2, 7.2 Hz), 0.14 (s, 9H)

The $^{13}$C NMR (100 MHz, CDCl$_3$) data of compound 15 are as follows.

δ 167.9, 107.1, 84.6, 53.3, 51.9, 33.9, 28.4, 27.1, 25.4, 19.5, 0.1

The results of mass spectrometry of compound 15 are as follows.

HRMS (ESI$^+$) calcd. for C$_{12}$H$_{25}$N$_2$Si (M+H$^+$), 237.1782; found, 237.1789.

[Chem. 29]

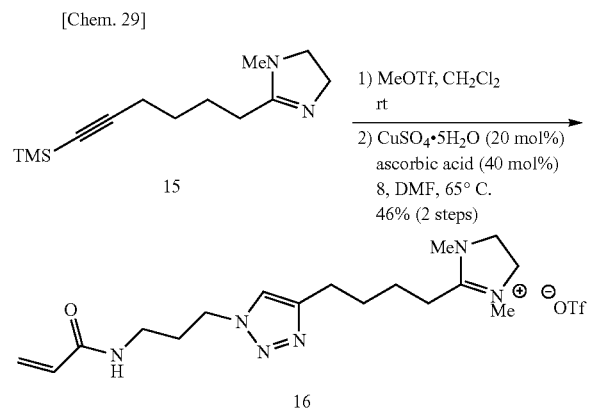

Imidazoline compound 15 (151 mg, 639 µmol) was dissolved in dichloromethane (3.19 mL), methyl trifluoromethanesulfonate (MeOTf) (145 µL, 1.28 mmol) was added thereto at room temperature, and the mixture was stirred for 3 hours. The solvent was removed under reduced pressure to obtain an imidazolium salt. The salt was dissolved in dimethylformamide (DMF) (3.0 mL), amide compound 8 (120 mg, 776 µmol), copper sulfate pentahydrate (CuSO$_4$.5H$_2$O) (31.9 mg, 127 µmol), and ascorbic acid (45.0 mg, 256 µmol) were added, and then the mixture was heated at 65° C. for 24 hours. The solvent was removed under reduced pressure to obtain the desired compound 16. The residue was purified by ODS silica gel chromatography (methanol/water=1/5 to 1/2), water was added to the desired fraction, and the mixture was washed three times with dichloromethane. The aqueous phase was recovered and concentrated under reduced pressure to obtain the desired acrylamide-based compound 16 as a brown solid (143 mg, 296 µmol, yield 46%).

The IR data of compound 16 are as follows.

IR (neat, cm$^{-1}$): 3352, 2936, 1660, 1624, 1553, 1467, 1281, 1157, 1031, 638

The $^1$H NMR (400 MHz, CDCl$_3$) data of compound 16 are as follows.

δ 7.93 (s, 1H), 7.43 (brs, 1H), 6.32 (d, 1H, J=9.2 Hz), 6.30 (d, 1H, J=2.8 Hz), 5.60 (dd, 1H, J=9.2, 2.8 Hz), 4.44 (t, 2H, J=6.4 Hz), 3.95 (s, 4H), 3.24 (dt, 2H, J=6.4, 6.4 Hz), 3.12 (s, 6H), 2.83 (t, 2H, J=6.4 Hz), 2.55 (t, 2H, J=8.0 Hz), 2.20 (tt, 2H, J=6.4, 6.4 Hz), 1.85 (tt, 2H, J=6.8, 6.8 Hz)

The $^{13}$C NMR (100 MHz, CDCl$_3$) data of compound 16 are as follows.

δ 168.4, 166.4, 146.1, 131.3, 125.8, 123.0, 49.9, 47.5, 36.0, 34.0, 29.8, 28.4, 24.6, 24.0, 23.9

The results of mass spectrometry of compound 16 are as follows.

HRMS (ESI$^+$) calcd. for C$_{17}$H$_{29}$N$_6$O (M$^+$), 333.2397; found, 333.2387.

Example B-2: Synthesis of a Linear Polymer Having the Identical Cationic Structure to the Novel Cationic Polymerization Initiator A heat-sensitive unit N-isopropylacrylamide (NIPAM), a cationic monomer unit compound 16, a fluorescent unit N-(2-{[7-(N,N-dimethylaminosulfonyl)-2,1,3-benzothiadiazol-4-yl]-(methyl)amino}methyl)-N-methylacrylamide (DBThD-AA), α,α'-azobisisobutyronitrile (AIBN), in the amounts shown in table 4, were dissolved in dimethylformamide (DMF) (5 mL), and dissolved oxygen was removed by passing argon gas through for 30 minutes. Then, the reaction was promoted at 60° C. for 8 hours, and the reaction mixture was cooled to room temperature. The solution was poured into diethyl ether (100 mL) with stirring. The resulting crystals were filtered, and after drying under reduced pressure, re-dissolved in methanol (MeOH) (1 mL) and re-precipitated, then dissolved in pure water, and purified by extensive dialysis using Visking tubing (cellulose tubing for dialysis) of 28.6 mm in diameter and 1000 mL of dialysis external fluid. The purified product was freeze-dried to obtain the title copolymers Lin40 and Lin41 as pale yellow powder. The yields are shown in table 4.

TABLE 4

The amounts of raw materials used for the synthesis of linear polymers, and the yield of the linear polymer obtained

| Compound name | NIPAM | Compound 16 | DBThD-AA | AIBN | Yield |
|---|---|---|---|---|---|
| Lin40 | 480 mM | 20 mM | 5 mM | 5 mM | 17% |
| Lin41 | 460 mM | 40 mM | 5 mM | 5 mM | 33% |

The results of characterization of copolymers Lin40 and Lin41 are shown in table 5. The ratio of NIPAM:cationic monomer unit (compound 16):DBThD-AA were, in this order,
Lin40, 94.5:5.48:1.43
Lin41, 93.0:7.03:1.43.
In addition, zeta potential measurements were conducted using 0.5 w/v % aqueous solution at 20° C.

TABLE 5

Characterization of the linear polymer obtained

| Compound name | $M_w$ | $M_n$ | $M_w/M_n$ | Zeta potential (mV) |
|---|---|---|---|---|
| Lin40 | 29,600 | 14,200 | 2.1 | 17.3 ± 1.0 |
| Lin41 | 27,800 | 12,600 | 2.2 | 22.7 ± 0.7 |

Example B-3: Temperature-Response Test of Lin40 and Lin41

Figure 4:
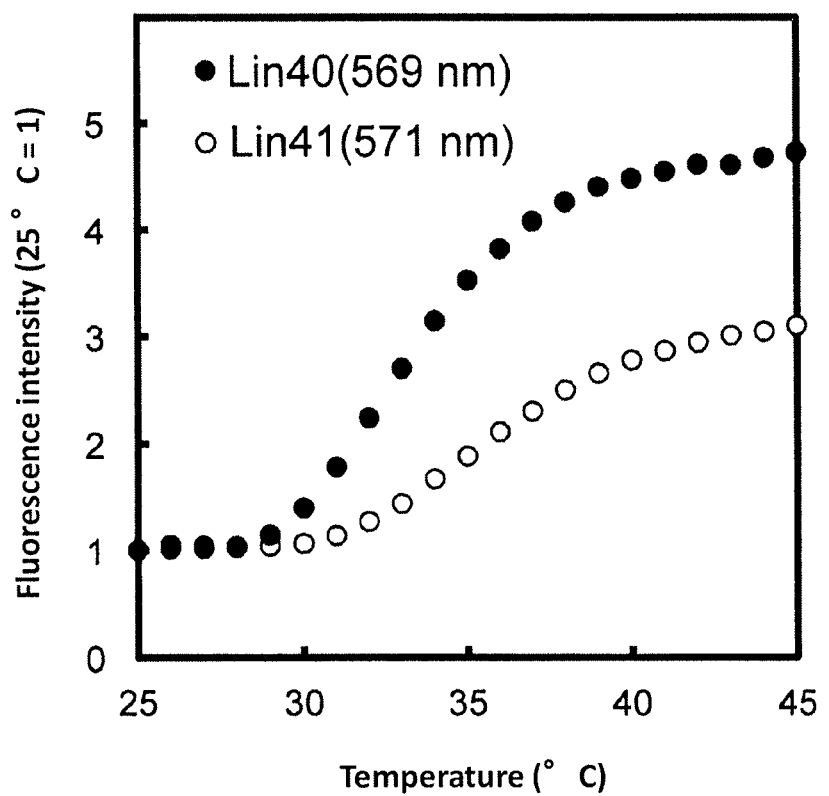
FIG. 4 An example of the results showing the heat-sensitive response test (0.005 w/v %, 450 nm excitation wavelength) of fluorescence intensities (Lin40: 569 nm, Lin41: 571 nm) of compounds Lin40 and Lin41 in aqueous 150 mM potassium chloride solution (black sphere: Lin40, white sphere: Lin41) (n=3).

A temperature-response test of Lin40 and Lin41 in an aqueous 150 mM potassium chloride (KCl) solution was performed as follows. The measurement was performed by using a JASCO FP-6500 spectrofluorophotometer, and an aqueous solution prepared by dissolving potassium chloride (KCl) purchased from Wako Pure Chemical Industry, Inc. in ultra-pure water as a solvent obtained from Milli-Q reagent system by Millipore, Inc. to make a concentration of 150 mM. In this experiment, the initial concentration of the compound was set to 0.005 w/v %, and the excitation wavelength to 450 nm. For the temperature control of the solution, JASCO ETC-273T water-cooled Peltier-type constant-temperature cell holder was used, and the temperature was measured by a thermocouple attached. The solution temperature was raised by 1° C. at a time, and the fluorescence spectra between 450-850 nm were measured at each temperature.
FIG. 4 shows examples of plotted fluorescence intensity change of Lin40 and Lin41 at 569 nm and 571 nm, respectively. From the result, it was found that probes that respond to temperature were also prepared using the newly synthesized cationic unit (compound 16). Additionally, it was found that, when the ratio of the cationic unit was increased, the fluorescence intensity rise in response to temperature change becomes smaller.

Example B-4: Synthesis of Various Temperature-Sensitive Probes

The synthesis of NN-AP4 (linear acrylamide-type polymer) was conducted following the method for AP4-FPT described in literature A (PLoS One, 2015, Vol. 10(2)). The synthesis of anion gel k40 was conducted following the method for DBThD nanogel described in literature B (Chemistry, A European Journal, 2012, Vol. 18, p 9552-9563).

Example 5: Introduction of a Temperature Probe into Animal Cells (Adherent Cells)

Figure 5:
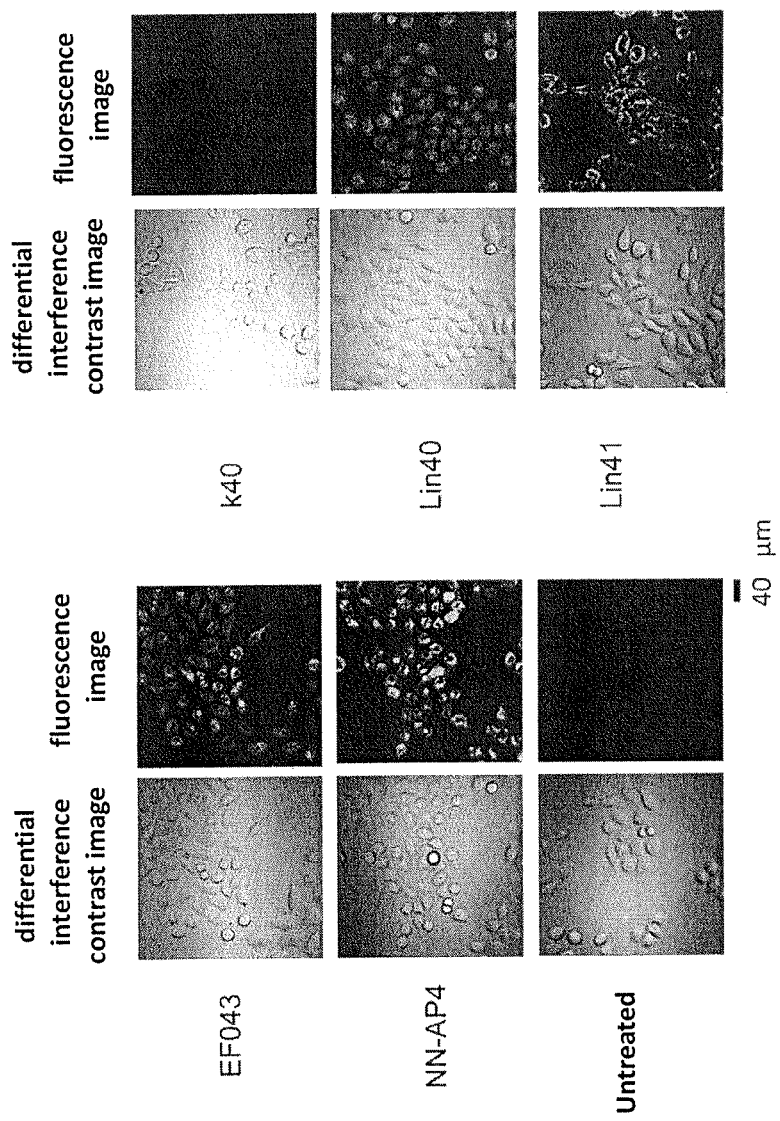
FIG. 5 An example of the pictures taken when EF043, NN-AP4, Lin40, Lin41 and k40 was individually mixed (37° C., 10 minutes) with human cervical carcinoma HeLa cells in 5% glucose solution and observed under a microscope (excitation light: 473 nm, fluorescence: 500-600 nm).
Figure 6:
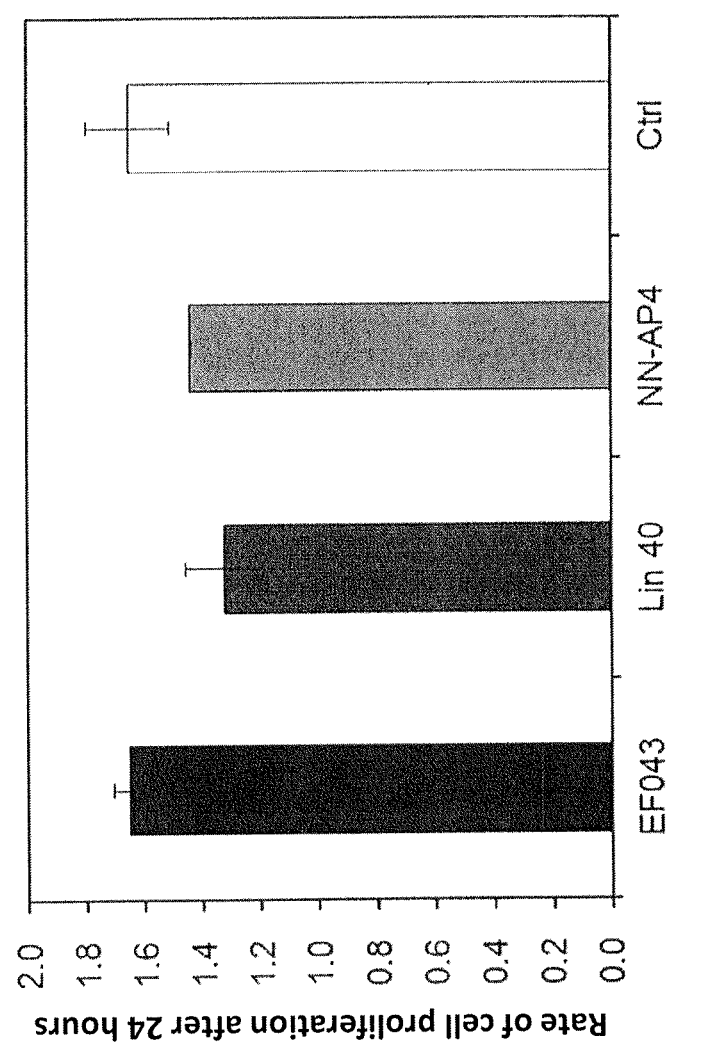
FIG. 6 An example of the results showing the evaluation of the proliferation rate by using the EF043-, NN-AP4-, or Lin40-introduced HeLa cells and counting the number of the probe-introduced cells 24 hours after introduction (n=3).

The human cervical carcinoma HeLa cells were inoculated in a dish with polymer coverslip bottom (ibidi Inc.) containing DMEM medium (10% FBS, 1% penicillin-streptomycin) and cultured. After 1 day, the medium was replaced with an aqueous 5% glucose solution, and each of EF043, NN-AP4, Lin40, Lin41, k40, was added such that the final concentration became 0.05% each, and the samples were left as it is at 37° C. for 10 minutes. Then, the probes were removed, and the cells were washed with phosphate buffered saline (PBS), transferred to phenolred-free DMEM medium, and observed under a microscope. The microscopic observation was conducted using a confocal laser microscope (FV1000, Olympus) and a 40× objective lens (Uplan Apo40×, NA0.85, Olympus). The cells were irradiated with a 473 nm laser (Multi Ar laser) to obtain 500-600 nm fluorescence images.
FIG. 5 shows some results of the photographed cells. The microscopic pictures obtained were processed to subtract the fluorescence intensity of the region with no cells as the background, and the cells that show more fluorescence signal than the own fluorescence of untreated cells were counted to calculate the rate of the probes introduced to the cells. The results are shown in FIG. 6. Although the temperature probe k40 prepared using a conventional polymerization initiator and has a negatively charged surface showed little introduction into the cell, the intracellular introduction of gel-type temperature probe EF043 and other probes that were prepared using new cationic polymerization initiators was confirmed. As for Lin41, its localization to the cell membrane was observed and its intracellular introduction was not very much.

TABLE 6

The rate of introduction of each temperature probe into the cells

| Probe | EF043 | Lin40 | Lin41 | k40 | NN-AP4 | Untreated |
|---|---|---|---|---|---|---|
| Introduction rate (%) | 91.8 ± 8.7 | 100.0 ± 0 | 45.4 ± 2.4 | 3.9 ± 3.9 | 98.7 ± 0.3 | 0 |

Note
1) "Untreated" is a control experiment in which no temperature probes were used.

Example 6: Evaluation of the Toxicity of Probes

As in example 5, EF043, NN-AP4, Lin40, and Lin41 were introduced into HeLa cells, and after being washed with phosphate buffered saline (PBS), the cells were transferred to a phenolred-free DMEM medium. Then, propidium iodide (PI), a non-permeable fluorescent reagent, was added to the medium such that the final concentration be 0.67 μg/mL, and after processing at 37° C. for 30 minutes, the sample was observed under a microscope. The fluorescence probe was excited by a 473 nm laser and propidium iodide (PI) was excited by a 559 nm laser, and observation was performed at 490-550 nm and 665-755 nm fluorescence wavelengths, respectively. The photomultiplier sensitivity and laser intensity of the camera used for observation were adjusted using methanol-treated cells as a control for dead cells.

Approximately 100 cells were selected among the cells that showed fluorescence from the temperature probes under a microscope, and the cells that showed fluorescence of propidium iodide (PI) was counted as the dead cells to calculate the survival percentage. The results are shown in Table 7. In EF043, Lin40, NN-AP4, little cytotoxicity derived from propidium iodide (PI) was observed, however, in Lin41, the cell membrane permeability was enhanced and PI was found to be cytotoxic. In other words, it became clear that in the case where temperature probes that are linear macromolecules are used, increasing the amount of cationic units introduced generates cytotoxicity.

TABLE 7

The cell survival rate (%) when each temperature probe was introduced into the cells

| EF043 | Lin40 | Lin41 | NN-AP4 | Ctrl |
|---|---|---|---|---|
| 100.0 ± 0 | 95.2 ± 1.9 | 87.5 ± 10.5 | 94.1 ± 3.1 | 99.6 ± 0.5 |

Note
1) "Ctrl" is a control experiment in which no temperature probes were used.

Example 7: Examination of the Effect of the Structure of the Temperature Probes on Cell Division Human cervical carcinoma HeLa cells were inoculated in a DMEM medium (10% FBS, 1% penicillin-streptomycin) in a polymer coverslip bottom dish with grids (μDish 35 mm grid-500) (ibidi, Inc.) and cultured. After 1 day, as in example 5, three probes, EF043, NN-AP4 and Lin40, were introduced, the samples were transferred to phenolred-free medium, and observed under a microscope. The microscopic observation was conducted using a confocal laser microscope (FV1000, Olympus) and a 40× objective lens (Uplan Apo40×, NA0.85, Olympus). The cells were irradiated by a 473 nm laser (Multi Ar laser) to obtain 500-600 nm fluorescence images.

Among the cells in a specific grid, those in which fluorescence probes were introduced were counted as in example 5, and after cultivation for 24 hours at 37° C. and under 5% $CO_2$, the cells in which fluorescence probes were introduced were re-counted to calculate cell proliferation rate after 24 hours.

The results are shown in FIG. 6. In the untreated control experiment (Ctrl), all the cells in which no probes were introduced were counted. As a result, it was found that the cationic gel EF043 showed nearly identical cell proliferation rate to that of control (Ctrl), and the linear temperature probes NN-AP4 and Lin40 inhibit cell proliferation. This inhibition effect does not depend on the structural difference of the cationic units (quaternary ammonium framework in NN-AP4, and 1,3-dimethyl-4,5-dihydro-1H-imidazol-3-ium frame in Lin40). In addition, since EF043 and Lin40 possess an identical structure of cationic molecule, it was found that the inhibition effect on the cell proliferation is greater when the macromolecule has a linear structure (Lin40) than the cell proliferation inhibition effect due to a cationic structure, and when it is gel-like (EF043) there is little inhibition effect. In addition, because the probe-introduced cells increased by incubation, it became clear that the probes were distributed to both cells upon division.

Example 8: Examination of the Effect on the Differentiation of the Brown Adipocyte The brown adipose tissues were harvested from a euthanized rat (Wistar, male, 3 weeks old), diced with scissors, suspended in a collagenase solution and incubated for 30 minutes at 37° C., with shaking with a stirrer. The undigested tissues were removed by a 100 μm cell strainer, the filtrate was centrifuged (400 g, room temperature, 5 minutes), and the pellets obtained were washed by suspending in HBSS (−) and centrifuged. They were suspended in hemolysis buffer, let stand for 10 minutes at room temperature, HBSS (−) was added and centrifuged, then the pellets were suspended in a proliferation medium (table 8), and filtered through a 40 μm cell strainer to provide SVF suspension. The SVF suspension was then inoculated to a glass bottom dish coated with collagen, and cultured at 37° C. After 18 hours, the medium was removed and the SVF cells were washed twice with HBSS (−), non-adhered cells were removed, a proliferation medium was added again and the cells were cultured for 4 days (37° C., 5% $CO_2$). Then, the cells were transferred to a differentiation medium (table 8) and after cultured for 48 hours (37° C., 5% $CO_2$), temperature-sensitive probe EF043 was introduced to the cells. The introduction was conducted by washing the cells with 5% glucose, then adding EF043 to the cells in 5% glucose such that the final concentration be 0.05 w/v %, and incubating at 37° C. for 15 minutes. Then, washed twice with HBSS, and the cells were observed under a microscope. Further, the EF043-introduced cells were transferred to a maintenance medium (table 8) which induces fat droplets, and after the cells were cultured for 3 days (37° C., 5% $CO_2$), they were observed under a microscope. The microscopic observation was conducted using a confocal laser microscope (FV1000, Olympus) and a 40× objective lens (Uplan Apo40×, NA0.85, Olympus). The cells were irradiated by a 473 nm laser (Multi Ar laser) to obtain 500-600 nm fluorescence images.

TABLE 8

The compositions of the proliferation medium, the differentiation medium, and the maintenance medium for the brown adypocytes.

| | Proliferation medium | Differentiation medium | Maintenance medium |
|---|---|---|---|
| Standard medium | DMEM (4500 mg/L Glc, pyruvate) | DMEM (4500 mg/L Glc, pyruvate) | DMEM (4500 mg/L Glc, pyruvate) |
| Serum | 10% FCS | 10% FCS | — |
| Ascorbic acid | 100 μM | 100 μM | 100 μM |
| Biotin | 33 μM | 33 μM | 33 μM |
| Pantothenic acid | 17 μM | 17 μM | 17 μM |
| Octanoic acid | 1 μM | 1 μM | 1 μM |
| Triiodothryronine (T3) | 50 nM | 50 nM | 50 nM |
| Penicillin | 100 U/mL | 100 U/mL | 100 U/mL |
| Streptomycin | 100 μg/mL | 100 μg/mL | 100 μg/mL |
| Insulin | — | 10 μg/mL | 0.1 nM |

TABLE 8-continued

The compositions of the proliferation medium, the differentiation medium, and the maintenance medium for the brown adypocytes.

| | Proliferation medium | Differentiation medium | Maintenance medium |
|---|---|---|---|
| Dexamethasone | — | 2.5 μM | — |
| IBMX | — | 0.5 mM | — |

Figure 7:
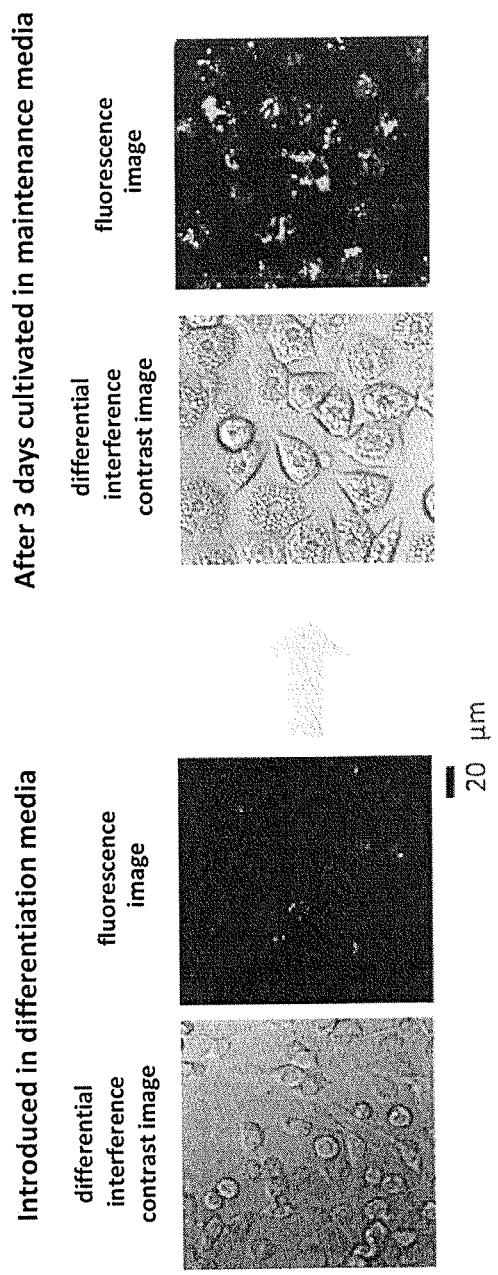
FIG. 7 An example of the results showing the brown adipocytes in a fully matured state observed under a microscope, wherein a cationic gel-type temperature probe EF043 was introduced into the brown adipocytes upon inducing differentiation and cultured for 3 days.

The results are shown in FIG. 7. As shown on the left in FIG. 7, the fluorescence from the temperature probe is seen in the cells after being cultured in the differentiation medium, therefore it was found that the probes are spontaneously taken up in the cells. When the cells are further cultured in a maintenance medium to promote the formation of fat droplets, as shown on the right in FIG. 7, it was shown that the fluorescence from the probes can be confirmed in the cells, and characteristic multilocular fat droplets are seen on brown adipocytes. From these results, it was found that the cationic gel-type temperature probe EF043 is maintained in the cell without inhibiting cell differentiation.

Example 9: Fluorescence Intensity Response of EF043 Against Cultured Cells (Floating Cells)

A sample of MOLT-4 (human acute leukemia T-lymphoblast cell) was cultured in a 100 mm dish using RPMI1640 medium (10% FBS) (inoculation $1 \times 10^4$ cells/mL). After 2 days, the culture broth 3 mL was centrifuged (300 g, 2 minutes) to remove the medium, after washing with 5% glucose, the cells were again re-suspended in 1 mL of 5% glucose, and EF043, NN-AP4 and Lin40 were added to the suspension such that the final concentration of each be 0.05%. After leaving the suspension at 37° C. for 10 minutes, the supernatant was removed by centrifugation (300 g, 2 minutes), the sample was washed with phosphate buffered saline (PBS), re-suspended in phosphate buffered saline (PBS), and non-permeable fluorescence reagent propidium iodide (PI) was added to the phosphate buffered saline (PBS) such that the final concentration be 0.67 μg/mL. After processing at 37° C. for 30 minutes, the cells were observed under a microscope. The fluorescence probes were excited by a 473 nm laser and propidium iodide (PI) was excited by a 559 nm laser, and observation was performed at 490-550 nm and 655-755 nm fluorescence wavelengths, respectively. Introduction of the probes was investigated by microscopic observation. The microscopic observation was conducted using a confocal laser microscope (FV1000, Olympus) and a 40× objective lens (Uplan SApo, Olympus). The cells were irradiated by a 473 nm laser (Multi Ar laser) to obtain 500-600 nm fluorescence images.

The probe-EF043-introduced MOLT-4 cells (that have not been treated with propidium iodide (PI)), suspended in phosphate buffered saline (PBS), were transferred to a cuvette, and a spherical stirrer 2 mm in diameter was added. The cuvette was placed in a JASCO FP-6500 spectrofluorometer, and fluorescence spectra were measured while stirring at approximately 800 rpm speed to prevent from the cells to sink. The excitation wavelength was set to 440 nm. For the control of the temperature, a JASCO ETC-273T water-cooled Peltier-type constant-temperature cell holder was used, and the temperature was measured by the thermocouple attached. The solution temperature was raised by 2° C. at a time, let stand for 2 minutes after raising the temperature to equilibrate the temperature inside and outside the cells, and the fluorescence intensity was measured at each temperature.

The introduction rate of the probe inside the cells was determined in the following way: first, the microscopic pictures obtained were processed to subtract the fluorescence intensity of the region with no cells as the background, and then the cells that show more fluorescence signal than their own fluorescence of untreated cells were counted to calculate the rate of the introduced probes to the cells. The toxicity of propidium iodide (PI) which indicates the cell membrane permeability was determined by first selecting 50-200 cells for which temperature probe fluorescence was observed under a microscope, and then counting the number of the cells for which fluorescence from propidium iodide (PI) was observed as the dead cells.

Figure 8:
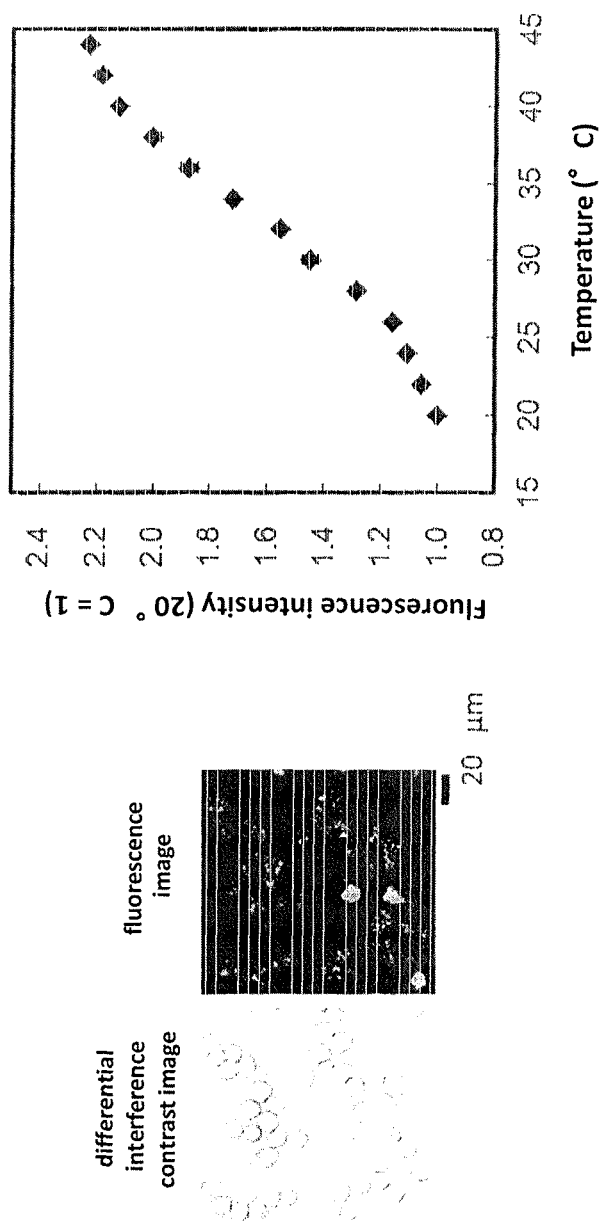
FIG. 8 An example of the pictures taken when the EF043 mixed (37° C., 10 minutes) with MOLT-4 (human acute leukemia T-lymphoblast cell) in 5% glucose solution (left) was observed under a microscope (excitation light: 473 nm, fluorescence: 500-600 nm), and an example of the results (n=3) showing the heat-sensitive response test of fluorescence intensities of EF043 in the MOLT-4 cells (right).

The results of the probe introduction rate and the propidium iodide (PI) toxicity test are shown in table 9, and the temperature response results are shown in FIG. 8. It became clear from the microscopic observation results that EF043 transfers into the cells just by mixing also with MOLT-4 cells. In terms of the toxicity of propidium iodide (PI), there was no difference among the probes used, and overall, no significant toxicity was observed.

Also, EF043 inside the cells responded sensitively to the external temperature changes, and raised the fluorescence intensity (fluorescence wavelength 570 nm) (FIG. 8). It was confirmed that the intracellular temperature can be measured in a wide temperature region of 25-40° C., the typical growth temperature of the mammalian cells.

TABLE 9

Intracellular introduction rate (%) of each temperature probe and evaluation of the toxicity of propidiunn iodide (PI)

| | EF043 | Lin40 | NN-AP4 | Ctrl |
|---|---|---|---|---|
| Introduction rate (%) | 99.1 ± 0.8 | 99.4 ± 0.9 | 89.3 ± 1.0 | 2.5 ± 1.1 |
| PI toxicity (%) | 1.2 ± 0.9 | 1.5 ± 0.8 | 1.9 ± 1.9 | 2.0 ± 0.1 |

Example 10: Testing of Heat-Sensitive Response of the Fluorescence Lifetime Change Using the suspension of the MOLT-4 cells in which the probe EF043 prepared in example 9 was introduced, heat-sensitive response of the fluorescence lifetime change was tested. FluoroCube 3000U (Horiba Jobin Yvon) time-correlated single photon counting fluorescence lifetime measurement equipment was used and the excitation wavelength was set at 405 nm. For excitation of a solution, LED (NanoLED-456, Horriba) was used and the fluorescence was measured at a pulse repetition rate of 1 MHz. For the solution temperature control, a JASCO ETC-273T water-cooled Peltier-type constant-temperature cell holder was used, and the thermometer attached was used to measure the temperature. Equilibration of the solution temperature was confirmed by a thermocouple before each measurement, and the fluorescence lifetime was measured at the fluorescence wavelength of 580 nm±8 nm. The fluorescence decay curve obtained was approximated with the following formula, to obtain fluorescence lifetime of two components.

$$I(t) = B_1 \exp(-t/\tau_1) + B_2 \exp(-t/\tau_2) \qquad \text{[Math. 1]}$$

From the fluorescence lifetime obtained, the average fluorescence lifetime at each temperature was calculated using the following formula.

$$\tau_f = (B_1\tau_1^2 + B_2\tau_2^2)/(B_1\tau_1 + B_2\tau_2) \quad \text{[Math. 2]}$$

Figure 9:
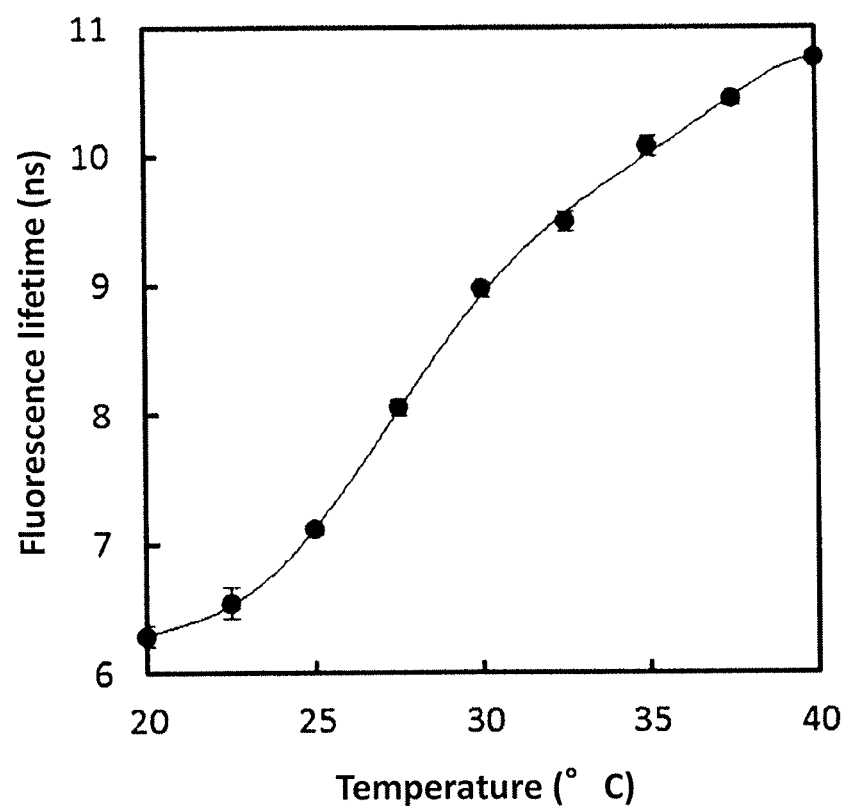
FIG. 9 An example of the results of the heat-sensitive response evaluation (n=3) of fluorescence lifetime of EF043 in MOLT-4 (human acute leukemia T-lymphoblast cell) cells.

The test results are shown in FIG. 9. The average fluorescence lifetime was found to be extended with increasing temperature, therefore it was confirmed that the average fluorescence lifetime changes sensitively in response to the temperature change.

Example 11: Evaluation of the Temperature Resolution

Consider a case where the temperature (T) is taken as x-axis and the fluorescence lifetime (τ) as y-axis, as in the result of example 10. When the minute amount is defined as ∝ and the error as δ, the following relationship is established.

$$\frac{\delta\tau}{\delta T} = \frac{\partial\tau}{\partial T} \quad \text{[Math. 3]}$$

Therefore, the temperature resolution δT which indicates a temperature difference it can detect is shown by $$\delta T = \left(\frac{\partial T}{\partial \tau}\right)\delta\tau \quad \text{[Math. 4]}$$

Since ∝ represents a minute amount herein, $$\left(\frac{\partial\tau}{\partial T}\right) \quad \text{[Math. 5]}$$

indicates the slope of the tangent of the curve in the graph in which the temperature (T) is set as x-axis and the fluorescence lifetime (τ) as y-axis. Since δ indicates the error, δτ is an error of the fluorescence lifetime. Herein, the standard deviation was used as the value of the error.

In other words, the temperature resolution can be calculated as (temperature resolution)=(reciprocal of the slope of the tangent of the curve in the graph in which the temperature (T) is set as x-axis and fluorescence lifetime (τ) as y-axis)×(fluorescence lifetime error).

Figure 10:
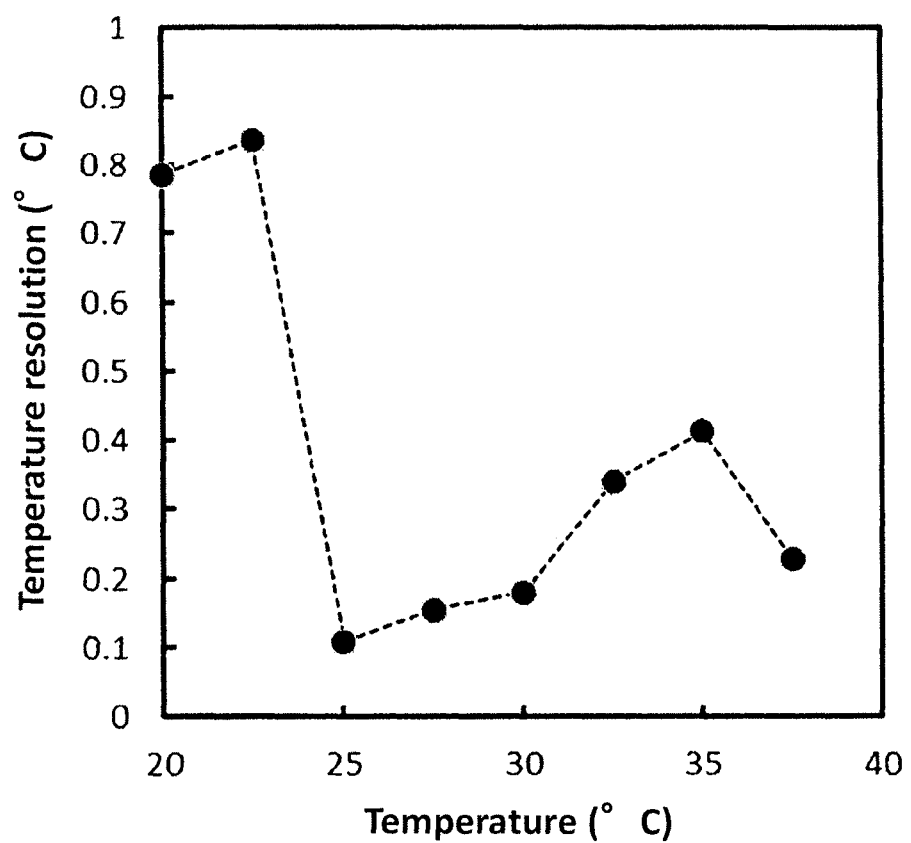
FIG. 10 An example of the results of the temperature resolution calculated from the graph in FIG. 9.

When the temperature resolution was calculated on FIG. 9, which is the results from example 10, FIG. 10 was obtained. EF043 is shown to have a temperature resolution of approximately 0.2° C., and was found to be highly quantitative.

Example 12: Application of PEG-Type Gels to the Cells

A sample of human embryonic kidney cells HEK293T was cultured in DMEM medium (10% FBS, 1% penicillin-streptomycin) in a 35 mm glass bottom dish (inoculation 1×10³ cells/cm²). After 1 day, the medium was replaced with 5% glucose, and compound 3G and fluorescein (1 μg/mL) or compound 3G and rhodamin B (0.5 μg/mL) were added such that the final concentrations of the fluorescent dyes be identical, and let stand at 37° C. for 15 minutes. Then, probes and fluorescent dyes were removed, and the cells were washed with phosphate buffered saline (PBS), transferred to a phenolred-free medium, and observed under a microscope. The microscopic observation was conducted using a confocal laser microscope (FV1000, Olympus). Fluorescein was excited by a 473 nm laser (Multi Ar laser), and rhodamin B was excited by a 559 nm laser, and fluorescence was observed. Approximately 20 cells were selected from the images obtained, average values of intracellular signals were calculated and were compared.

Figure 11:
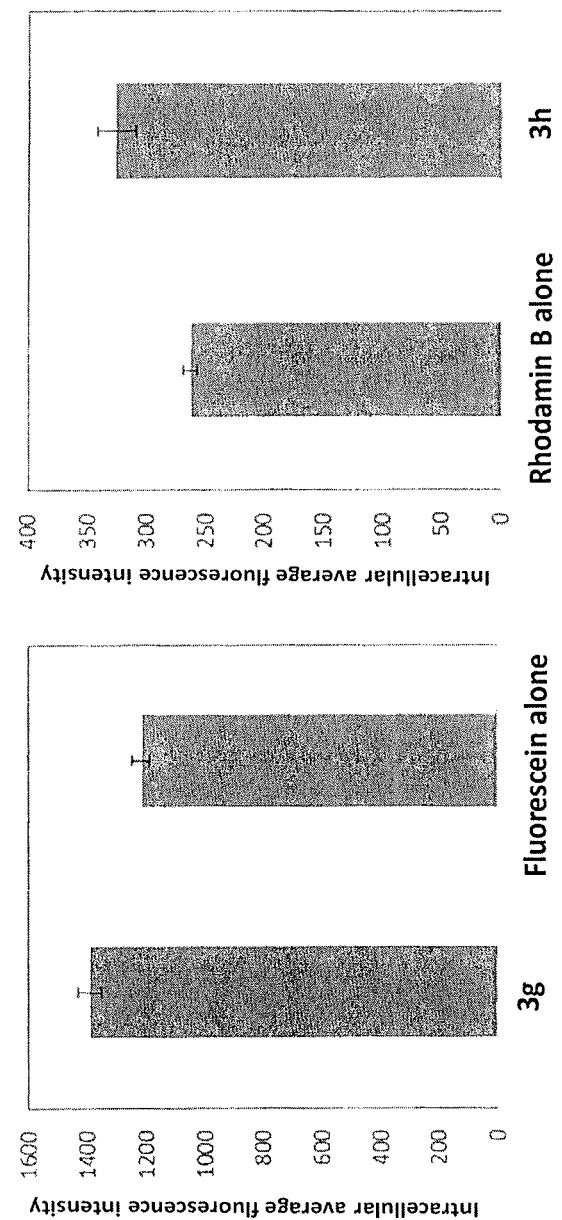
FIG. 11 An example of the results of a comparison between the delivery efficiency into HEK293T (human embryonic kidney cells) cells of PEG-type cationic gel containing fluorescein and rhodamin B, and that of fluorescent molecules alone (n=3).

The results are shown in FIG. 11. It was found that the introduction rate into the cells is higher when the fluorescent dyes are embedded in cationic gels than the fluorescent dyes alone. This phenomenon was observed in both as a molecule negatively charged fluorescein and as a molecule positively charged rhodamin B, suggesting that intracellular uptake was promoted without being affected by the characters of molecules to be embedded. In other words, these cationic gels can also be used for intracellular delivery technique of small molecules as well as other molecules.

The invention claimed is:

1. A compound having a chemical structure represented by general formula (I):

[Chem. 1]

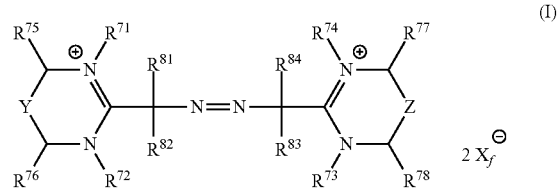

wherein
Y represents a single bond or CHR⁸⁵,
Z represents a single bond or CHR⁸⁶,
$R^{72}$ and $R^{73}$ are each independently selected from $C_{1-6}$ alky group,
$R^{75}$, $R^{76}$, $R^{77}$, $R^{78}$, $R^{85}$ and $R^{86}$ are each independently selected from the group consisting of a hydrogen atom, $C_{1-6}$ alkyl group, $C_{1-6}$ alkoxy group, $C_{1-6}$ alkylcarbonyl group, phenyl group and hydroxyl group, wherein said $C_{1-6}$ alkyl group, $C_{1-6}$ alkoxy group, $C_{1-6}$ alkylcarbonyl group and phenyl group are optionally substituted with 1 or 2 substituents selected from the group consisting of $C_{1-6}$ alkyl group, $C_{1-6}$ alkoxy group, $C_{1-6}$ alkylcarbonyl group, phenyl group and hydroxyl group,
or
$R^{75}$ and $R^{76}$ or $R^{77}$ and $R^{78}$ together optionally form —(CH₂)₃₋₅—,
$R^{81}$, $R^{82}$, $R^{83}$ and $R^{84}$ are a substituent selected from the group consisting of $C_{1-4}$ alkyl group, $C_{1-4}$ alkylcarbonyl group and $C_{1-3}$ alkoxy group, wherein the $C_{1-4}$ alkyl is optionally substituted with one $C_{1-3}$ alkoxy group; and
$R^{71}$ and $R^{74}$ each independently are $C_{1-3}$ alkyl group, and $X_f^-$ is counter anion.

2. The compound according to claim 1, wherein said Y and Z represent single bond.

3. The compound according to claim 1, wherein said $R^{81}$, $R^{82}$, $R^{83}$, and $R^{84}$ are each independently selected from the group consisting of methyl group, ethyl group, methylcarbonyl group, isobutyl group, and 2-methyl-2-methoxypropyl group.

4. The compound according to claim 1, wherein said $R^{71}$ and $R^{74}$ are a methyl group.

5. The compound according to claim 1, wherein said $R^{72}$ and $R^{73}$, said $R^{75}$ and $R^{77}$, said $R^{76}$ and $R^{78}$, said $R^{81}$ and $R^{84}$, said $R^{82}$ and $R^{83}$, and said $R^{71}$ and $R^{74}$, each represent an identical substituent, and said Y and Z represent an identical substituent or a single bond.

6. The compound according to claim 1, wherein said $R^{71}$, $R^{72}$, $R^{73}$, $R^{74}$, $R^{81}$, $R^{82}$, $R^{83}$, and $R^{84}$ are a methyl group, and said $R^{75}$, $R^{76}$, $R^{77}$ and $R^{78}$ are a hydrogen atom, and said Y and Z are a single bond.

7. A cationic polymerization initiator, comprising the compound according to claim 1.

8. A method for producing an intracellular delivery vehicle, comprising performing a radical polymerization reaction involving the cationic polymerization initiator according to claim 7, a monomer comprising carbon-carbon double bonds, and a crosslinker.

* * * * *